(12) United States Patent
Shinohara et al.

(10) Patent No.: US 7,579,374 B2
(45) Date of Patent: Aug. 25, 2009

(54) AGENT FOR IMPROVING BONE METABOLISM

(75) Inventors: Gou Shinohara, Yokosuka (JP); Kin-ya Tsuchiya, Yokosuka (JP); Katsuaki Yamanouchi, Yokosuka (JP); Toshiyuki Inui, Yokosuka (JP)

(73) Assignee: The Nisshin OilliO Group, Ltd., Chuo-ku, Tokyo (JP)

( * ) Notice: Subject to any disclaimer, the term of this patent is extended or adjusted under 35 U.S.C. 154(b) by 327 days.

(21) Appl. No.: 10/669,470

(22) Filed: Sep. 25, 2003

(65) Prior Publication Data

US 2004/0058995 A1 Mar. 25, 2004

Related U.S. Application Data

(63) Continuation of application No. PCT/JP02/03187, filed on Mar. 29, 2002.

(30) Foreign Application Priority Data

Mar. 30, 2001 (JP) ............................. 2001-101821

(51) Int. Cl.
*A01N 37/02* (2006.01)
*A61K 31/33* (2006.01)
(52) U.S. Cl. ...................................... 514/522
(58) Field of Classification Search ................ 554/224; 514/560
See application file for complete search history.

(56) References Cited

U.S. PATENT DOCUMENTS

| | | | |
|---|---|---|---|
| 4,642,314 A * | 2/1987 | Tahara et al. | 514/475 |
| 4,738,801 A * | 4/1988 | Tahara et al. | 554/223 |
| 5,618,558 A | 4/1997 | Horrobin et al. | |
| 5,663,461 A * | 9/1997 | Mori et al. | 568/886 |
| 5,888,541 A | 3/1999 | Horrobin et al. | |

FOREIGN PATENT DOCUMENTS

| | | |
|---|---|---|
| EP | 0 261 814 | 3/1988 |
| EP | 0 711 749 A1 | 5/1996 |
| JP | 44-4651 | 2/1944 |
| JP | 59-001446 | 1/1984 |
| JP | 4-253908 A | 9/1992 |
| JP | 7-215849 | 8/1995 |
| JP | 11-130670 | 5/1999 |
| JP | 2001-158736 | 6/2001 |
| WO | WO 96/34846 | 11/1996 |
| WO | 99/67809 | * 12/1999 |
| WO | WO 99/67809 | 12/1999 |
| WO | WO9967809 | * 12/1999 |
| WO | WO 00/21524 | 4/2000 |

OTHER PUBLICATIONS

Yasuko Koshihara, "Vitamin K and Bone Metabolism," Bulletin of Oil & Fat Chemical Society, 1996, pp. 435-443, vol. 45, No. 5, Japan.
Naoyuki Takahashi et al., "Osteoblastic Cells Are Involved In Osteoclast Formation," The Endocrine Society, 1988, pp. 2600-2602, vol. 123, No. 5, USA.
Hidehiko Hibino et al., "N-3 Polyunsaturated Fatty Acids and Bone Metabolism: Beneficial Effects of Eicosapentaenoic Acid," Bulletin of Oil & Fat Chemical Society, 2000, pp. 1391-1399, vol. 49, Nos. 11 and 12, Japan.
Young Li, et al., "Conjugated Linoleic Acids Alter Bone Fatty Acid Composition and Reduce ex vivo Prostaglandin $E_2$ Biosynthesis in Rats Fed n-6 or n-3 Fatty Acids," Lipids, 1998, pp. 417-425, vol. 33, No. 4, USA.
Y. Koshihara et al., "Vitamin $K_2$ Promotes $1\alpha,25(OH)_2$ Vitamin.$D_3$-Induced Mineralization in Human Periosteal Osteoblasts," Calcified Tissue International, 1996, pp. 59:466-473, USA.

* cited by examiner

*Primary Examiner*—Deborah D Carr
(74) *Attorney, Agent, or Firm*—Buchanan Ingersoll & Rooney PC

(57) ABSTRACT

The present invention relates to an improver for bone metabolism comprising one or at least two of chain isoprenoid fatty acid esters and preferably to an improver for bone metabolism whose improving effect is ascribable to the bone absorption-inhibitory action and/or the bone formation-promoting action of the esters.

9 Claims, No Drawings

AGENT FOR IMPROVING BONE METABOLISM

This application is a continuation of International Application No. PCT/JP02/03187 filed on Mar. 29, 2002, and claims priority under 35 U.S.C. §§119 and/or 365 to 2001-101821 filed in Japan on Mar. 30, 2001, the entire content of which is hereby incorporated by reference.

BACKGROUND OF THE INVENTION

The present invention relates to an improver for bone metabolism, which comprises chain isoprenoid fatty acid esters as the active ingredient, which is excellent in the bone metabolism-improving effect and absorbability, safety and which is advantageous in the price and the present invention also relates to a food or beverage for the improvement of the bone metabolism.

Recently, the average span of life of the human being has gradually been increased due to the progress in, for instance, medical science. Correspondingly, in the society having a high rate of aged persons, which is attendant on the increase of the span of life, how to spend and enrich the life in the senescence (the quality of life) would be quite important for the aged persons. To enrich their life, it is essential that the aged persons are sound in their minds and bodies and, to this end, it is a key or principal subject to develop any means for impeding or arresting the aging. There have been described a variety of aging phenomena based on the foregoing standpoints and the osteoporosis as a representative senile disease has attracted special interest recently. In particular, the osteoporosis is a systemic disease in which the bone gets fragile and the patient attacked by the same easily suffers a fractured bone. This would be a disease, which constitutes a variety of social problems. For instance, this may correspondingly cause the fracture of collum femoris and the compression fracture of the spine, which are accompanied by severe pains, and the patient may become a bedridden (old) man because of such a fracture of bone.

In the normal condition, the bone always repeats remodeling thereof to thus maintain the equilibrium in the bone metabolism. More specifically, the bone is replaced with fresh one with a period ranging from 120 to 150 days, without accompanying any change in the amount thereof, while maintaining a good balance between the system (bone absorption system) for destroying and absorbing tissues, which are calcified by the osteoclasts for the supplementation of the calcium component required for the life conservation activities from the bone to the blood and the system (osteogenesis (bone forming) system), in which the osteoblasts and osteocytes deposit collagen and/or calcium, as bone substrates, onto the bone. In the osteoporosis, however, there exists abnormality in such bone metabolism or the bone absorption ability gets ahead of the osteogenetic function and this may lead to the reduction in the amount of the bone and the bone gets fragile. In particular, in the women after their menopause, the function of secreting and forming the female hormone, which has a bone absorption-inhibitory action and an osteogenesis-promoting action, is rapidly impaired and accordingly, they are quite susceptible to the abnormality in the bone metabolism and they lose their balance between the bone absorption ability and the osteogenetic function. For this reason, they are liable to suffer from the osteoporosis. In fact, one out of three women of 45-year-old or older has already suffered from the osteoporosis or the considerable reduction in the amount of the bone. Therefore, materials having an effect of improving or eliminating such abnormality in the bone metabolism may be expected as prophylactic agents or therapeutic agents for the diseases related to bone such as osteoporosis.

It has previously been recommended to ingest a sufficient amount of calcium, vitamin D and vitamin K in the form of a diet from the viewpoint of the improvement of the bone metabolism and the prevention of osteoporosis. At present, however, one should care about his eating habit in order to efficiently ingest these nutrients and only persons who fear to suffer from such diseases have improved their eating habit. Moreover, these nutrients have also commercially been supplied or distributed in the form of health foods such as tablets and supplements, but there have not yet been solved many problems concerning, for instance, absorbability, stability and price of these nutrients. In view of the present status, there has been desired for the development of a material, which has a bone metabolism-improving effect and an osteoporosis-prophylactic effect, which can efficiently be absorbed, which is stable and which can be provided at a low price.

Up to now, there have been developed, for instance, Estrogen, Calcitonin, Ipriflavone, activated vitamin D3, Bisphosphonate and Vitamin K2 as therapeutic agents for treating the osteoporosis. However, these conventional therapeutic agents suffer from a variety of drawbacks or cause various harmful side effects, respectively. For Instance, the administration of Estrogen results in bleeding like the menstruation (false menstruation), becomes a cause of some unpleasant feelings such as swelling of the breast and may increase the incidence of a disease such as breast cancer (mastocarcinoma). Calcitonin is a peptide and it can only be administered through injection. The administration of Ipriflavone may bring about gastro-intestinal disorders. Activated vitamin D3 may induce hypercalcemia and may cause urolithiasis and disorders of digestive organs. The administration of Bisphosphonate may likewise inhibit the osteogenetic function of patients. Vitamin K2 also shows a blood coagulation effect and therefore, the administration thereof is limited to specific patients. In addition, all of these therapeutic agents are not sufficient in the establishment of the balance between the efficacy as pharmaceutical agents and the convenience or their price. For this reason, there has recently been focused attention on the development of novel pharmaceutical agents and foods and beverages developed from such standpoints.

DISCLOSURE OF THE INVENTION

It is accordingly an object of the present invention to provide an agent for improving the bone metabolism, which is excellent in the bone metabolism-improving effect, absorbability and safety, and which is advantageous in the price and it is also an object of the present invention also to provide an improver for bone metabolism as well as a food or beverage for improving the bone metabolism, which can be administered through either oral or parenteral route.

The inventors of this invention have conducted various studies to accomplish the foregoing objects, have found that chain isoprenoid fatty acid esters show a bone metabolism-improving effect identical or superior to that achieved by vitamin K2 as an anti-osteogenetic agent, that these esters have high absorbability and safety and that they are not expensive and have thus completed the present invention.

According to the present invention, there is provided an improver for bone metabolism comprising, as the active ingredient, chain isoprenoid fatty acid esters represented by the following general formula (I) and preferably an improver for bone metabolism, the effect of which is based on the bone absorption-inhibitory action and/or osteogenesis-promoting action:

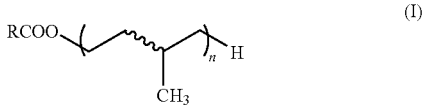

wherein, R represents an arbitrary hydrocarbon functional group, the wavy line means a single or double bond and n represents an integer ranging from 1 to 14, provided that when n is 2 or higher, the wavy lines may be the same or different.

In this respect, the fatty acids as the constituents of the chain isoprenoid fatty acid esters are not restricted to specific ones insofar as they have carbon atom numbers falling within the range of from 2 to 30. The fatty acid is preferably one having 8 to 22 carbon atoms and more preferably 14 to 22 carbon atoms. Examples of such fatty acids include linear saturated fatty acids, linear unsaturated fatty acids, branched fatty acids, hydroxy-fatty acids, epoxy-fatty acids, keto-fatty acids and cyclic fatty acids. Among these, preferred are linear fatty acids from the viewpoint of the abundance thereof in nature and the bone metabolism-improving effect and, in particular, preferably used herein include linear unsaturated fatty acids such as n-6 type unsaturated fatty acids, n-3 type unsaturated fatty acids and conjugated fatty acids. Specific examples of such n-6 type unsaturated fatty acids are preferably linoleic acid, α-linolenic acid, bis-homo-γ-linolenic acid and arachidonic acid; specific examples of n-3 type unsaturated fatty acids are preferably α-linolein, stearidonic acid, eicosatetraenoic acid, eicosapentaenoic acid, docosapentaenoic acid and docosahexaenoic acid; and specific examples of conjugated fatty acids are preferably conjugated linoleic acid and α-eleostearic acid.

Moreover, the improver for bone metabolism preferably comprises chain isoprenoid fatty acid esters represented by the foregoing general formula (I) wherein n=2 to 4 from the viewpoint of the bone metabolism-improving effect, more preferably the improver for bone metabolism comprises chain isoprenoid fatty acid esters represented by the foregoing general formula (I) wherein n=4 and particularly preferably the improver for bone metabolism comprises chain isoprenoid fatty acid esters selected from the group consisting of geranyl-geranyl fatty acid esters, phytyl fatty acid esters and dihydrophytyl fatty acid esters. In this respect, the fatty acids are the same as those discussed above.

The present invention also relates to an inhibitor for bone absorption comprising chain isoprenoid fatty acid esters represented by the foregoing general formula (I).

The present invention further relates to a promoter for bone formation (osteogenesis) comprising chain isoprenoid fatty acid esters represented by the foregoing general formula (I).

The present invention likewise relates to a method of using the foregoing improver for bone metabolism and more specifically to a method of the therapeutic use of the same as a pharmaceutical agent as well as methods of the daily use thereof by the administration through oral and subcutaneous routes. Accordingly, the present invention also relates to an improver for bone metabolism comprising chain isoprenoid fatty acid esters represented by the foregoing general formula (I) and externally applied to the skin.

The improver for bone metabolism according to the present invention is effective for the prophylaxis and/or treatment of diseases related to any abnormality of the bone metabolism, but the agent of the present invention is preferably used for the purpose of the prophylaxis and/or treatment of osteoporosis.

Accordingly, the present invention likewise relates to an agent for preventing and/or treating osteoporosis, which comprises, as the active ingredient, chain isoprenoid fatty acid esters represented by the foregoing general formula (I).

The present invention also relates to a food or beverage for improving bone metabolism comprising, as the active ingredient, chain isoprenoid fatty acid esters represented by the foregoing general formula (I).

BEST MODE FOR CARRYING OUT THE INVENTION

The present invention relates to an improver for bone metabolism comprising, as the active ingredient, chain isoprenoid fatty acid esters represented by the following general formula (I) and preferably an improver for bone metabolism, the effect of which is based on the bone absorption-inhibitory action and/or osteogenesis-promoting action of the compound:

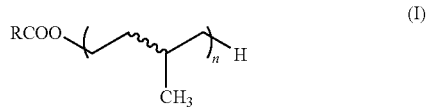

wherein —OOCR represents a derivable ester group such as an ester group capable of being derived from a chain isoprenoid alcohol and one of a variety of fatty acids, R represents an arbitrary hydrocarbon functional group, the wavy line means a single or double bond and n represents an integer ranging from 1 to 14, provided that when n is 2 or higher, the wavy lines may be the same or different.

In the general formula (I), R is not limited to any specific one inasmuch as it is a hydrocarbon functional group derived from a fatty acid having 2 to 30 carbon atoms. In particular, the group is preferably a hydrocarbon functional group derived from a fatty acid having 8 to 22 carbon atoms and more preferably one derived from a fatty acid having 14 to 22 carbon atoms. In this respect, the fatty acids may be one selected from the group consisting of linear saturated fatty acids such as acetic acid, butyric acid, caproic acid, caprylic acid, capric acid, undecanoic acid, lauric acid, tridecanoic acid, myristic acid, pentadecanoic acid, palmitic acid, margaric acid, stearic acid, nonadecanoic acid, arachidic acid, behenic acid, lignoceric acid, cerotic acid, montanic acid and melissic acid; linear unsaturated fatty acids, for instance, monounsaturated fatty acids such as obtusilic acid, linderic acid, tsuzuic acid, palmito-oleic acid, oleic acid, elaidic acid, vaccenic acid, cis-vaccenic acid, petroselinic acid, gadoleic acid, eicosenoic acid, erucic acid, cetoleic acid, nervonic acid, ximenic acid and lumepueic acid; n-3 type unsaturated fatty acids such as α-linolenic acid, stearidonic acid, eicosatetraenoic acid, eicosapentaenoic acid, docosapentaenoic acid and docosahexaenoic acid; n-6 type unsaturated fatty acids such as linoleic acid, linoelaidic acid, γ-linolenic acid, bis-homo-γ-linolenic acid and arachidonic acid; conjugated fatty acids such as conjugated linoleic acid and α-eleostearic acid; fatty acids carrying double bonds at the 5-position thereof such as pinolenic acid, sciadonic acid, juniperic acid and columbinic acid; polyvalent unsaturated fatty acids, other than those listed above, such as hiragonic acid, moroctic acid, clupanodonic acid and nishinic acid; branched fatty acids such as isobutyric acid, isovaleric acid, iso acid and anti-iso acid; hydroxy fatty acids such as α-hydroxy acid, β-hydroxy acid, mycolic acid and polyhydroxy acid; epoxy-fatty acids;

keto-fatty acids; and cyclic fatty acids. Among these, preferred are linear fatty acids from the viewpoint of the abundance thereof in nature and the bone metabolism-improving effect and, in particular, preferably used herein include linear unsaturated fatty acids such as n-6 type unsaturated fatty acids, n-3 type unsaturated fatty acids and conjugated fatty acids. Specific examples of such n-6 type unsaturated fatty acids preferably include linoleic acid, γ-linolenic acid, bis-homo-γ-linolenic acid and arachidonic acid; specific examples of n-3 type unsaturated fatty acids preferably include α-linolein, stearidonic acid, eicosatetraenoic acid, eicosapentaenoic acid, docosapentaenoic acid and docosahexaenoic acid; and specific examples of conjugated fatty acids preferably include conjugated linoleic acid and α-eleostearic acid.

Moreover, the improver for bone metabolism preferably comprises chain isoprenoid fatty acid esters represented by the foregoing general formula (I) wherein n=2 to 4 from the viewpoint of the bone metabolism-improving effect, more preferably the improver for bone metabolism comprises chain isoprenoid fatty acid esters represented by the foregoing general formula (I) wherein n=4 and particularly preferably the improver for bone metabolism comprises chain isoprenoid fatty acid esters selected from the group consisting of geranyl-geranyl fatty acid esters, phytyl fatty acid esters and dihydrophytyl fatty acid esters. In this respect, the fatty acids are the same as those listed and discussed above.

The present invention also relates to an inhibitor for bone absorption comprising chain isoprenoid fatty acid esters represented by the foregoing general formula (I).

The present invention further relates to a promoter for bone formation (osteogenesis) comprising chain isoprenoid fatty acid esters represented by the foregoing general formula (I).

The foregoing chain isoprenoid fatty acid esters are not particularly restricted in their origins and may, for instance, be those naturally occurring ones and artificially synthesized ones. In this respect, these esters are relatively abundant in plants as natural resources and therefore, they are preferably those derived from plants. In case where they are artificially prepared, they may be prepared according to a chemical synthesis, an enzyme reaction or fermentation using microorganisms, with the method, which makes use of an enzyme reaction, being particularly preferred since it is simple and convenient.

The improver for bone metabolism according to the present invention is effective for the prophylaxis and/or treatment of diseases related to any abnormality of the bone metabolism, but the agent of the present invention is preferably used for the purpose of the prophylaxis and/or treatment of osteoporosis, among others. Accordingly, the present invention likewise relates to an agent for preventing and/or treating osteoporosis, which comprises, as the active ingredient, chain isoprenoid fatty acid esters represented by the foregoing general formula (I).

The present invention likewise relates to a method of using the foregoing improver for bone metabolism and more specifically to a method of the therapeutic use of the same as a pharmaceutical agent as well as methods of the daily use thereof by the administration through oral and subcutaneous routes.

The present invention also relates to a food or beverage comprising, as the active ingredient, chain isoprenoid fatty acid esters represented by the foregoing general formula (I).

The present invention relates to an improver for bone metabolism comprising chain isoprenoid fatty acid esters represented by the general formula (I) (hereunder referred to as "isoprenoid ester(s)"). In this connection, the term "improver for bone metaboism" used herein means an agent used for the improvement of the bone metabolism and, in particular, the term includes both the improver for bone metabolism used as a final drug and the improver for bone metabolism used as a component of other products such as pharmaceutical agents, foods and beverages, feeds and cosmetic products. It is difficult to definitely and specifically distinguish one from the other, but the former mainly includes those formulated under the thoroughly controlled conditions and whose components and composition are specified, while the latter includes ingredients whose components and composition are not completely elucidated or specified such as crude products, as well.

The food and beverage of the present invention may include a variety of foods and beverages such as confectionery, processed foods (food preparations), blend oils and fats, foods prepared by adding oils and fats to food materials (food preparations comprising oils and fats), dairy products, and various beverages. The food and beverage of the present invention are not particularly restricted in their shape and properties and may be in any state, for instance, a solid, hemi-solid, gel-like, liquid or powdery state.

The present invention relates to an improver for bone metabolism, an inhibitor for bone absorption, a promoter for n osteogenesis, an agent for preventing and/or treating osteoporosis and a food or beverage for the improvement of the bone metabolism, which comprise an isoprenoid ester represented by the general formula (I). In this connection, the term "chain isoprenoid fatty acid ester" means an ester having a structure formed as a result of the dehydration condensation of a chain isoprenoid alcohol and a fatty acid from the viewpoint of the structure thereof. The chain isoprenoid alcohol in general has a chain-like structure obtained through the binding of a plurality of isoprene units each having 5 carbon atoms and carries a hydroxyl group. Moreover, the ester derivative used herein means one capable of being formed from the hydroxyl group of a chain isoprenoid alcohol with the carboxyl group of a fatty acid.

The present invention relates to an improver for bone metabolism. In this regard, the term "bone metabolism-improving effect" means an effect of improving the condition in which the balance between the bone absorption system in which osteoclasts are involved and the osteogenetic system in which osteoblasts are involved is destroyed to thus maintain the equilibrium of the bone metabolism.

The isoprenoid esters incorporated into the improver for bone metabolism of the present invention possess a bone absorption-inhibitory effect. The term "bone absorption" used herein means a bone dissolution-like action by the osteoclasts for the supplementation of calcium from the bone to the blood, observed when the calcium concentration in the blood is reduced. Accordingly, the improver for bone metabolism of the present invention can show its bone absorption-inhibitory effect by directly inhibiting the formation of osteoclasts, which govern the bone-absorption or by indirectly inhibiting the activity of the osteoclasts. In the usual bone remodeling, the amount of the bone absorption is roughly equal to the amount of the bone formed. In the bone-exhausted state in, for instance, the osteoporosis, however, the balance between the foregoing systems is destroyed and more specifically, the bone-formation is not promoted at all in response to the increment of the bone absorption or the bone absorption is not inhibited at all in response to the reduction of the bone formation. In such cases, the improver for bone metabolism of the present invention would inhibit any excess bone absorption through its bone absorption-inhibitory effect to thus eliminate the condition in which the desired metabolic balance between the bone absorption and the bone formation is put into disorder.

The foregoing bone absorption-inhibitory effect of the isoprenoid esters included in the improver for bone metabolism according to the present invention would be responsible for the presence of, in particular, the side chains of the chain isoprenoid This is also supported by, for instance, the fact that vitamin K2 and chain isoprenoid alcohols, in particular, geranyl geraniol or the like show excellent bone absorption effects (see, for instance, Japanese Un-Examined Patent Publication (hereunder referred to as "J.P. KOKAI") Hei 7-215849 and Hei 11-130670; Bulletin of Oil & Fat Chemical Society in Japan, 1996, Vol. 45, No. 5, pp. 435-443).

In fact, the bone absorption-inhibitory effect of the isoprenoid esters incorporated into the improver for bone metabolism of the present invention can be demonstrated by the osteoclast-formation-inhibitory action in a coexisting cell culture (co-culture) system. The cell co-culture system used herein means a system in which osteoblasts and hematopoietic cells are subjected to co-culture in the presence of a factor for promoting the formation of osteoclasts and which thus easily permits the analysis of the differentiation process of the osteoclasts (Endocrinology, 1988, 123: 2600-2602). In such a system, osteoclasts are formed and therefore, the degree of osteoclast-formation can be evaluated by the determination of a tartaric acid-resistant acid phosphatase (TRACP) activity in the cell layer as the parameter indicative of the osteoclast.

When an isoprenoid ester is added to the foregoing coexisting cell culture system, the TRACP activity is in general reduced as compared with a control (a system free of any added isoprenoid ester). In other words, it is clear that the isoprenoid esters incorporated into the improver for bone metabolism of the present invention show their bone absorption-inhibitory effect by directly inhibiting the formation of osteoclasts, which govern the bone-absorption or by indirectly inhibiting the activity of the osteoclasts. In the usual bone remodeling, the amount of the bone absorption is roughly equal to the amount of the bone formed. Moreover, the bone absorption-inhibitory effects of the isoprenoid esters are identical or superior to those observed for vitamin Ks (in particular, Vitamin K2 (MK-4)), which have generally been known to have bone metabolism-improving effects.

The isoprenoid esters incorporated into the improver for bone metabolism according to the present invention possess a bone formation-promoting action. The term "bone formation" used herein means the action by the osteoblasts or the formation of a bone substrate and the calcification thereof. Therefore, the improver for bone metabolism according to the present invention can likewise show a bone absorption-promoting effect through the promotion of the proliferation of osteoblasts and the activation of the osteoblasts. In the usual bone remodeling, the amount of the bone absorption is roughly identical to that of the bone formed. In the bone-exhausted state in, for instance, the osteoporosis, however, the balance between the foregoing systems is destroyed and more specifically, the bone-formation is not promoted at all in response to the increment of the bone absorption or the bone absorption is not inhibited at all in response to the reduction of the bone formation. In such cases, the improver for bone metabolism of the present invention would improve or enhance the bone-forming ability, which has been impaired, through its bone formation-promoting action to thus eliminate the condition in which the desired metabolic balance between the bone absorption and the bone formation is put into disorder.

The foregoing bone formation-promoting action of the isoprenoid esters incorporated into the improver for bone metabolism of the present invention is ascribable, in particular, to the fatty acid side chains thereof. This is also supported by, for instance, the fact that eicosapentaenoic acid (Bulletin of Oil & Fat Chemical Society in Japan, 2000, Vol. 49, Nos. 11 and 12, pp. 1391-1399) and conjugated linoleic acid (Lipids, 1998, Vol. 33, No. 4, pp. 417-425) possess excellent bone formation-promoting effects.

Indeed, the bone formation-promoting effects of the isoprenoid esters incorporated into the improver for bone metabolism of the present invention can be demonstrated by the osteoblast growth-promoting effect observed in a cell culture system (Calcif. Tissue Int., 1996, 59: 466-473). In such a system, the osteoblasts are proliferated and the activity of osteoblasts is increased. Therefore, any influence of a substance on the osteoblast-formation can be evaluated by determining, for instance, the rate of cell proliferation and the alkaline phosphatase (ALP) activity as an activity parameter.

When the isoprenoid esters, which are incorporated into the improver for bone metabolism of the present invention, are added to the foregoing cell culture system, the rate of cell proliferation is increased as compared with a control (a system free of any added isoprenoid ester). In other words, it is clear that the isoprenoid esters used in the present invention show an effect of promoting the proliferation of osteoblasts involved in the bone formation or osteogenesis. Contrary to this, Vitamin K2 (MK-4), which has generally been known to possess a bone metabolism-improving effect, reduces the rate of cell proliferation in the same cell culture system and when the concentration thereof added is high, it may exert a harmful effect on the cell to thus result in the extinction of the cells. From the foregoing, the isoprenoid esters used in the present invention may serve to promote the osteoblast and one can guess that they are quite safe.

When the isoprenoid esters, which are incorporated into the improver for bone metabolism of the present invention, are added to the foregoing cell culture system, the ALP activity is in general improved as compared with a control (a system free of any added isoprenoid ester). In other words, it would be recognized that the isoprenoid esters incorporated into the improver for bone metabolism of the present invention also show an effect of improving the activity of osteoblasts.

As has been discussed above, the improver for bone metabolism of the present invention particularly possesses either or both of the bone absorption-inhibitory action originated from the chain isoprenoid side chains or the bone formation-promoting action originated from the fatty acid side chains and these actions are quite favorable for the improvement of the balance of the bone metabolism. In particular, it would be quite preferred that the agent possesses both of these actions, since these actions may synergistically be utilized for the improvement of the balance of the bone metabolism. Moreover, the bone absorption-inhibitory and bone formation-promoting actions are originated from the chain isoprenoid side chains and the fatty acid side chains of the foregoing esters, respectively and therefore, the kinds of these chain isoprenoid side chains and fatty acid side chains can appropriately be selected or designed to thus design the desired bone absorption-inhibitory and bone formation-promoting actions of each particular isoprenoid ester.

In this regard, the fatty acid moieties or functional groups constituting the isoprenoid esters represented by the general formula (I) are not restricted to particular ones inasmuch as the carbon atom number thereof falls within the range of from 2 to 30. In particular, preferred such functional groups are preferably those derived from fatty acids having 8 to 22 carbon atoms and such functional groups are more preferably those derived from fatty acids having 14 to 22 carbon atoms. Specific examples of such fatty acids are linear saturated fatty acids such as acetic acid, butyric acid, caproic acid, caprylic acid, capric acid, undecanoic acid, lauric acid, tridecanoic acid, myristic acid, pentadecanoic acid, palmitic acid, margaric acid, stearic acid, nonadecanoic acid, arachidic acid, behenic acid, lignoceric acid, cerotic acid, montanic acid and melissic acid; linear unsaturated fatty acids, for instance, monounsaturated fatty acids such as obtusilic acid, linderic acid, tsuzuic acid, palmito-oleic acid, oleic acid, elaidic acid, vaccenic acid, cis-vaccenic acid, petroselinic acid, gadoleic acid, eicosenoic acid, erucic acid, cetoleic acid, nervonic acid, ximenic acid and lumepueic acid; n-3 type unsaturated fatty acids such as α-linolenic acid, stearidonic acid, eicosatetraenoic acid, eicosapentaenoic acid, docosapentaenoic acid and docosahexaenoic acid; n-6 type unsaturated fatty acids such as linoleic acid, linoelaidic acid, γ-linolenic acid, bis-homo-γ-linolenic acid and arachidonic acid; conjugated fatty acids such as conjugated linoleic acid and α-eleostearic acid; fatty acids carrying double bonds at the 5-position thereof such as pinolenic acid, sciadonic acid, juniperic acid and columbinic acid; polyvalent unsaturated fatty acids, other than those listed above, such as hiragonic acid, moroctic acid, clupanodonic acid and nishinic acid; branched fatty acids such as isobutyric acid, isovaleric acid, iso acid and anti-iso acid; hydroxy fatty acids such as α-hydroxy acid, β-hydroxy acid, mycolic acid and polyhydroxy acid; epoxy-fatty acids; keto-fatty acids; and cyclic fatty acids.

As the foregoing fatty acids, preferably used herein are linear fatty acids, in particular, because of their abundance in nature. Further there is such a tendency that the presence of a double bond may accelerate the bone formation and therefore, preferred are linear unsaturated fatty acids, in particular, monounsaturated fatty acids such as palmito-oleic acid, oleic acid, vaccenic acid and erucic acid; n-6 type unsaturated fatty acids such as linoleic acid, γ-linolenic acid, bis-homo-γ-linolenic acid and arachidonic acid; n-3 type unsaturated fatty acids such as α-linolenic acid, stearidonic acid, eicosatetraenoic acid, eicosapentaenoic acid, docosapentaenoic acid and docosahexaenoic acid; and conjugated fatty acids such as conjugated linoleic acid and α-eleostearic acid.

The foregoing fatty acids preferably used herein from the viewpoint of their bone metabolism-improving effect, in particular, the bone formation-promoting effect include, for instance, n-6 type unsaturated fatty acids such as linoleic acid, γ-linolenic acid, bis-homo-γ-linolenic acid and arachidonic acid; n-3 type unsaturated fatty acids such as α-linolenic acid, stearidonic acid, eicosatetraenoic acid, eicosapentaenoic acid, docosapentaenoic acid and docosahexaenoic acid; and conjugated fatty acids such as conjugated linoleic acid and α-eleostearic acid.

Chain isoprenoid alcohols usable in the preparation of the isoprenoid esters used in the present invention are not particularly restricted in their origins and may, for instance, be those naturally occurring ones and artificially synthesized ones. In this respect, these alcohols are relatively abundant in plants as natural resources and therefore, they are preferably those derived from plants. Specific examples thereof are geraniol, farnesol, geranyl geraniol, phytol and dihydrophytol. Among them, geranyl geraniol, phytol and dihydrophytol are preferred.

The chain isoprenoid alcohols constituting the isoprenoid esters used in the present invention have structures realized by reducing isoprenoid esters represented by the general formula (I). In Formula (I), when n is 2 or higher, the wavy lines may be the same or different. In other words, alcohols used for the preparation of the isoprenoid esters used in the present invention may have one or at least two single bonds and one or at least two double bonds. Examples of such alcohols are phytol and dihydrophytol. Specific examples of alcohols, which may be used in the present invention, are geraniol, farnesol, geranyl geraniol, phytol and dihydrophytol. Preferably used herein include geranyl geraniol, phytol and dihydrophytol, among others.

The chain isoprenoid alcohols usable in the preparation of the isoprenoid esters used in the present invention are not particularly restricted in their origins and may, for instance, be those naturally occurring ones and artificially synthesized ones. In this respect, these alcohols are relatively abundant in plants as natural resources and therefore, they are preferably those derived from plants. More specifically, preferred are plants serving as raw materials of oils and fats, with oils and fats derived from plants being more preferred. Such plant's oils and fats are not restricted to any particular one, but specific examples thereof preferably used herein are crude soybean oil, crude rapeseed oil, crude cotton seed oil, crude sunflower oil, crude safflower oil, crude sesame oil, olive oil, crude linseed oil, crude rice bran oil, palm oil, cacao butter and kapok oil, with plant's oils and fats such as crude sesame oil and crude linseed oil being particularly preferred.

The chain isoprenoid ester included in the improver for bone metabolism of the present invention is a highly safe compound. The chain isoprenoid is a precursor formed during the biosynthesis of, for instance, cholesterol, steroid or tocopherol in a living body, while the fatty acids are substances essential for living bodies. These facts also demonstrate that they have considerably high safety.

Such a high safety of the chain isoprenoid ester can likewise be confirmed by determining the LD50 value thereof observed when it is administered to an animal. Indeed, the LD50 value thereof was found to be not less than 2000 mg/kg body weight.

The isoprenoid esters incorporated into the improver for bone metabolism of the present invention have a bone metabolism-improving effect identical or superior to those observed for a series of vitamin Ks whose bone metabolism-improving effect has currently been known, as has been described above. In other words, these esters have an osteoclast growth-inhibitory action and a bone formation-promoting action identical or superior to those observed for vitamin Ks. In addition, the isoprenoid esters used in the present invention serve to promote the proliferation of osteoblast and do not show any cytotoxicity at all, unlike vitamin Ks. Moreover, regarding the production cost or the supply of these substances, vitamin Ks are quite expensive, while the isoprenoid esters used in the present invention can be prepared at a low production cost. When the foregoing are put together, the isoprenoid esters used in the present invention are quite preferred substances even when they are compared with vitamin K.

In addition, the isoprenoid esters used in the present invention are ester derivatives of fatty acids and therefore, they are highly fat-soluble. For this reason, when they are used in oil systems or emulsified systems, they can be handled like the usual oil-soluble components. Moreover, they are almost tasteless, odorless and colorless and therefore, the use thereof is quite favorable since they are not limited in taste, odor and color. In other words, they can be used in a variety of applications without any trouble.

The isoprenoid esters used in the present invention are quite favorable from the viewpoint of absorbability since they are, on the whole, fat-soluble and therefore, it would be expected that they are absorbed together with oils. Thus, it would be predicted that they are absorbed along with oil components, which are, by nature, excellent in the absorbability and accordingly, they are preferably used in oil systems or emulsion systems. The present invention is not restricted to the following, but it would be expected that they may be absorbed in the body along with oil components, when they are, for instance, used in foods or beverages, in particular, they are used in the form of blend oils or foods prepared by adding oils and fats to food materials. In addition, it would be expected that when they are used in oily agents externally applied to the skin such as ointments, they are efficiently be absorbed through the skin.

Moreover, the improver for bone metabolism of the present invention preferably comprises an isoprenoid ester represented by Formula (I) wherein n=2 to 4, in particular, n=4 while taking into consideration the bone metabolism-improving effect, in particular, both of the strength of the bone absorption-inhibitory effect and easy availability of the ester and more specifically, the improver for bone metabolism preferably comprises isoprenoid esters selected from the group consisting of geranyl-geranyl fatty acid esters, phytyl fatty acid esters and dihydrophytyl fatty acids.

Such geranyl-geranyl fatty acid esters, phytyl fatty acid esters and dihydrophytyl fatty acids used herein mean the isoprenoid esters represented by Formula (I) wherein n=4 and which are different, from one another, in the number and position of double bonds, but it is known that these esters are present in trace amounts in nature. In the present invention, the isoprenoid esters may be any one including either naturally occurring ones or artificially synthesized ones, but naturally occurring ones are preferably used in the present invention while taking into consideration, for instance, any influence thereof on the human body and the feeling of security upon its practical use. On the other hand, artificially synthesized ones are preferably used while taking into consideration the stable supply.

Examples of geranyl-geranyl fatty acid esters include, but are not limited to, geranyl-geranyl acetate, geranyl-geranyl butyrate, geranyl-geranyl caproate, geranyl-geranyl caprylate, geranyl-geranyl caprate, geranyl-geranyl undecanoate, geranyl-geranyl laurate, geranyl-geranyl tridecanoate, geranyl-geranyl myristate, geranyl-geranyl pentadecanoate, geranyl-geranyl palmitate, geranyl-geranyl margarate, geranyl-geranyl stearate, geranyl-geranyl nonadecanoate, geranyl-geranyl arachidate, geranyl-geranyl behenate, geranyl-geranyl lignocerate, geranyl-geranyl cerotate, geranyl-geranyl montanate, geranyl-geranyl melissic acid ester, geranyl-geranyl obtusilic acid ester, geranyl-geranyl linderic acid ester, geranyl-geranyl tsuzuic acid ester, geranyl-geranyl palmito-oleate, geranyl-geranyl oleate, geranyl-geranyl elaidate, geranyl-geranyl vaccenate, geranyl-geranyl cis-vaccenate, geranyl-geranyl petroselinic acid ester, geranyl-geranyl gadoleic acid ester, geranyl-geranyl eicosenoic acid ester, geranyl-geranyl erucic acid ester, geranyl-geranyl cetoleic acid ester, geranyl-geranyl nerbonate, geranyl-geranyl ximenic acid ester, geranyl-geranyl lame-citrate, geranyl-geranyl α-linolenate, geranyl-geranyl stearidonate, geranyl-geranyl eicosatetraenoate, geranyl-geranyl eicosapentaenoate, geranyl-geranyl docosapentaenoate, geranyl-geranyl docosahexaenoate, geranyl-geranyl linoleate, geranyl-geranyl linoelaidic acid ester, geranyl-geranyl γ-linolenate, geranyl-geranyl bis-homo-γ-linolenate, geranyl-geranyl arachidonate, geranyl-geranyl conjugated linoleate, geranyl-geranyl α-eleostearate, geranyl-geranyl pinolenic acid ester, geranyl-geranyl sciadonic acid ester, geranyl-geranyl juniperic acid ester, geranyl-geranyl columbinic acid ester, geranyl-geranyl hiragonate, geranyl-geranyl moroctate, geranyl-geranyl clupanodonate, geranyl-geranyl nishinic acid ester, geranyl-geranyl isobutyrate, geranyl-geranyl isovalerate, geranyl-geranyl iso acid ester, geranyl-geranyl anti-iso acid ester, geranyl-geranyl α-hydroxy acid ester, geranyl-geranyl β-hydroxy acid ester, geranyl-geranyl mycolic acid ester, geranyl-geranyl polyhydroxy acid ester, geranyl-geranyl epoxy-fatty acid esters, geranyl-geranyl keto-fatty acid esters and geranyl-geranyl cyclic fatty acid esters. Among these geranyl-geranyl fatty acid esters, preferred are geranyl-geranyl caprylate, geranyl-geranyl caprate, geranyl-geranyl laurate, geranyl-geranyl myristate, geranyl-geranyl palmitate, geranyl-geranyl stearate, geranyl-geranyl oleate, geranyl-geranyl α-linolenate, geranyl-geranyl eicosapentaenoate, geranyl-geranyl docosahexaenoate, geranyl-geranyl linoleate, geranyl-geranyl γ-linolenate and geranyl-geranyl conjugated linoleate.

Examples of phytyl fatty acid esters include, but are not limited to, phytyl acetate, phytyl butyrate, phytyl caproate, phytyl caprylate, phytyl caprate, phytyl undecanoate, phytyl laurate, phytyl tridecanoate, phytyl myristate, phytyl pentadecanoate, phytyl palmitate, phytyl margarate, phytyl stearate, phytyl nonadecanoate, phytyl arachidate, phytyl behenate, phytyl lignocerate, phytyl cerotate, phytyl montanate, phytyl melissic acid ester, phytyl obtusilic acid ester, phytyl linderic acid ester, phytyl tsuzuic acid ester, phytyl palmito-oleate, phytyl oleate, phytyl elaidate, phytyl vaccenate, phytyl cis-vaccenate, phytyl petroselinic acid ester, phytyl gadoleic acid ester, phytyl eicosenoic acid ester, phytyl erucic acid ester, phytyl cetoleic acid ester, phytyl nervonate, phytyl ximenic acid ester, phytyl lumepueate, phytyl α-linolenate, phytyl stearidonate, phytyl eicosatetraenoate, phytyl eicosapentaenoate, phytyl docosapentaenoate, phytyl docosahexaenoate, phytyl linoleate, phytyl linoelaidic acid ester, phytyl γ-linolenate, phytyl bis-homo-γ-linolenate, phytyl arachidonate, phytyl conjugated linoleate, phytyl α-eleostearate, phytyl pinolenic acid ester, phytyl sciadonic acid ester, phytyl juniperic acid ester, phytyl columbinic acid ester, phytyl hiragonate, phytyl moroctate, phytyl clupanodonate, phytyl nishinic acid ester, phytyl isobutyrate, phytyl isovalerate, phytyl iso acid ester, phytyl anti-iso acid ester, phytyl α-hydroxy acid ester, phytyl β-hydroxy acid ester, phytyl mycolic acid ester, phytyl polyhydroxy acid ester. phytyl epoxy-fatty acid esters, phytyl keto-fatty acid esters and phytyl cyclic fatty acid esters. Among these phytyl fatty acid esters, preferred are phytyl caprylate, phytyl caprate, phytyl laurate, phytyl myristate, phytyl palmitate, phytyl stearate, phytyl oleate, phytyl α-linolenate, phytyl eicosapentaenoate, phytyl docosahexaenoate, phytyl linoleate, phytyl γ-linolenate and phytyl conjugated linoleate.

Examples of dihydrophytyl fatty acid esters include, but are not restricted to, dihydrophytyi acetate, dihydrophytyl butyrate, dihydrophytyl caproate, dihydrophytyl caprylate, dihydrophytyl caprate, dihydrophytyl undecanoate, dihydrophytyl laurate, dihydrophytyl tridecanoate, dihydrophytyl myristate, dihydrophytyl pentadecanoate, dihydrophytyl palmitate, dihydrophytyl margarate, dihydrophytyl stearate, dihydro-phytyl nonadecanoate, dihydrophytyl arachidate, dihydrophytyl behenate, dihydro-phytyl lignocerate, dihydrophytyl cerotate, dihydrophytyl montanate, dihydrophytyl melissic acid ester, dihydrophytyl obtusilic acid ester, dihydrophytyl linderic acid ester, dihydrophytyl tsuzuic acid ester, dihydrophytyl palmito-oleate, dihydrophytyl oleate, dihydrophytyl elaidate, dihydrophytyl vaccenate, dihydrophytyl cis-vaccenate, dihydro-phytyl petroselinic acid ester, dihydrophytyl gadoleic acid ester, dihydrophytyl eicosenoic acid ester, dihydrophytyl erucic acid ester, dihydrophytyl cetoleic acid ester, dihydrophytyl nervonate, dihydrophytyl ximenic acid ester, dihydrophytyl lumepueate, dihydrophytyl α-linolenate, dihydrophytyl stearidonate, dihydrophytyl eicosatetra-enoate, dihydrophytyl eicosapentaenoate, dihydrophytyl docosapentaenoate, dihydro-phytyl docosahexaenoate, dihydrophytyl linoleate, dihydrophytyl linoelaidic acid ester, dihydrophytyl γ-linolenate, dihydrophytyl bis-homo-γ-linolenate, dihydrophytyl arachidonate, dihydrophytyl conjugated linoleate, dihydrophytyl α-eleostearate, dihydrophytyl pinolenic acid ester, dihydrophytyl sciadonic acid ester, dihydrophytyl juniperic acid ester, dihydrophytyl columbinic acid ester, dihydrophytyl hiragonate, dihydrophytyl moroctate, dihydrophytyl clupanodonate, dihydrophytyl nishinic acid ester, dihydrophytyl isobutyrate, dihydrophytyl isovalerate, dihydrophytyl iso acid ester, dihydrophytyl anti-iso acid ester, dihydrophytyl α-hydroxy acid ester, dihydrophytyl β-hydroxy acid ester, dihydrophytyl mycolic acid ester, dihydrophytyl polyhydroxy acid ester, dihydrophytyl epoxy-fatty acid esters, dihydrophytyl keto-fatty acid esters and dihydrophytyl cyclic fatty acid esters. Among these dihydrophytyl fatty acid esters, preferred are dihydrophytyl caprylate, dihydrophytyl caprate, dihydrophytyl laurate, dihydrophytyl myristate, dihydrophytyl palmitate, dihydrophytyl stearate, dihydrophytyl oleate, dihydrophytyl α-linolenate, dihydrophytyl eicosapentaenoate, dihydrophytyl docosahexaenoate, dihydrophytyl linoleate, dihydrophytyl γ-linolenate and dihydrophytyl conjugated linoleate.

These isoprenoid esters are present in a variety of plant bodies in nature and therefore, they can be obtained from these plant bodies through, for instance, extraction. Such plant bodies as raw materials are not restricted to specific ones, but the isoprenoid esters are highly fat-soluble (lipid-soluble) and therefore, preferred examples thereof are crude oils of plants since they have high contents of such esters and they are available in large quantities at relatively low prices. When using crude plant's oils as raw materials for these esters, the method for the preparation thereof using these materials is not restricted to any particular one, but these isoprenoid esters can be extracted or isolated and purified by, for instance, a solvent extraction method, a method, which makes use of the difference in solubility between the esters and impurities, a fractional precipitation method and a liquid chromatography method, which may be used alone or in any appropriate combination or may repeatedly be used.

In particular, the esters derived from geranyl geraniol, phytol and dihydrophytol with a variety of fatty acids are widely present in the natural world and, in particular, they are present in plant bodies in relatively large quantities. For this reason, preferred examples of raw materials used for the preparation of the foregoing substances are naturally occurring plants although such raw materials are not restricted to particular ones. Further, such raw materials are preferably plants serving as raw materials for oils and fats while taking into consideration the fat-solubility of the foregoing substances and the raw materials are more preferably oils and fats derived from plants. Examples of such plant's oils and fats include, but are not limited to crude soybean oil, crude rapeseed oil, crude cotton seed oil, crude sunflower oil, crude safflower oil, crude sesame oil, olive oil, crude linseed oil, crude rice bran oil, palm oil, cacao butter and kapok oil, with plant's oils and fats such as crude sesame oil, crude linseed oil, crude soybean oil and crude rapeseed oil being particularly preferred, in consideration of the contents of these substances. These plant's oils and fats as well as raw materials therefor have already widely been distributed and therefore, they are preferably used herein from the viewpoint of the stable supply thereof. Moreover, the isoprenoid esters represented by Formula (I) and used in the present invention can likewise be prepared from products generated during the processes for the production of these plant's oils such as compressed residues, extraction residues, oil-expression residues, compressed oils, extracted oils, degumming oil lees, deoxidation oil cake, dark oils, waste decoloring agents, deodorization scum, oil-extraction juices, waste water and waste filter mediums. Among these products, preferred are, for instance, waste decoloring agents and deodorization scum. The esters derived from geranyl geraniol, phytol and dihydrophytol with a variety of fatty acids can be obtained by, for instance, extracting from the foregoing raw materials with, for instance, solvents, which are further preferably subjected to concentration and/or fractionation-purification procedures, with highly purified products or isolated ones being particularly preferred. In the present invention, any product obtained in or during these processes can be used without any problem. In this regard, the methods for, for instance, the foregoing extraction, or concentration and/or fractionation-purification are not restricted to specific ones. However, specific examples thereof include a solvent extraction method, a method, which makes use of the difference in solubility between the esters and impurities, a fractional precipitation method and a liquid chromatography method, which may be used alone or in any appropriate combination or may repeatedly be used for the extraction, or concentration and/or fractionation-purification of these isoprenoid esters.

More specifically, examples of such extraction solvents are water; known hydrophilic organic solvents, for instance, alcohols such as methyl alcohol, ethyl alcohol, glycerin, propylene glycol and 1,3-butylene glycol, acetone, tetrahydrofuran, acetonitrile, 1,4-dioxane, pyridine, dimethyl sulfoxide, N,N-dimethylformamide and acetic acid; and known hydrophobic organic solvents such as hexane, cyclohexane, carbon tetrachloride, chloroform, dichloromethane, 1,2-dichloroethane, diethyl ether, ethyl acetate, benzene, toluene, heptane and isooctane. In addition, these organic solvents may be used alone or in any combination of at least two of them. Among these organic solvents, preferred are hydrophobic organic solvents, with hexane, diethyl ether, heptane and isooctane being particularly preferred.

The conditions for the extraction are not restricted to specific ones, but the extraction is carried out at a temperature ranging from 5 to 95° C., preferably 10 to 90° C. and more preferably 15 to 85° C. and the extraction may suitably be carried out even at ordinary temperature as well. The extraction may suitably be carried out under ordinary pressure, under the application of a pressure or under reduced pressure established by, for instance, aspiration. Moreover, these isoprenoid esters may be extracted according to, for instance, the shaking extraction and using an extraction machine provided with a stirring device in order to improve the extraction efficiency. The extraction time may vary depending on the other extraction conditions, but it preferably ranges from several minutes to several hours.

The amount of the solvent used in this extraction ranges from 1 to 100 times (mass/mass ratio, those in the following description are shown in the same way also) and preferably 1 to 20 times the amount of the raw material.

The solvent and moisture can be removed by any known method such as distillation under reduced pressure, drying under a vacuum or a reduced pressure, freeze-drying or lyophilization and spray drying.

Specifically, after the foregoing raw material for plant's oil is extracted with a hydrophobic organic solvent, a part or the whole of the hydrophobic organic solvent is removed from the resulting extract, water is, if needed, added to the extract and the aqueous phase is then removed to concentrate the extract and to thus give isoprenoid esters represented by Formula (I) and used in the present invention.

Alternatively, the hydrophilic organic solvent is removed from the extract derived from the foregoing raw material for plant's oil, followed by optional addition of water to the remaining aqueous solution and then addition of a hydrophobic organic solvent thereto for the liquid-liquid partition in a water-hydrophobic organic solvent system to concentrate the extract and to thus give isoprenoid esters represented by Formula (I) and used in the present invention. In this connection, the amount of water to be added upon the liquid-liquid partition is not limited to specific ones inasmuch as it permits the effective partition, but it preferably ranges from 1 to 100 times, more preferably 5 to 50 times and further preferably 10 to 30 times the mass of the extract evaporated to dryness.

In addition, the overall content of the isoprenoid esters represented by Formula (I) and used in the present invention, which are present in an extract obtained from, for instance, oil-expression residues obtained in the plant's oil-production processes is preferably not less than 95% and more preferably 95 to 99.99%. This overall content can be determined by, for instance, the gas chromatography technique. Moreover, the foregoing isoprenoid esters can artificially be prepared as well. The method for artificially preparing the same is not restricted to any specific one, but specific examples thereof include chemical synthesis methods, a method, which makes use of an enzyme reaction and a method in which the esters are produced using, for instance, microorganisms.

In particular, the isoprenoid esters can quite simply and safely prepared from chain isoprenoid alcohols and triglycerides, diglycerides, monoglycerides, fatty acids, fatty acid methyl esters, fatty acid ethyl esters or the like according to the transesterification reactions using an enzyme such as lipase and carboxyl esterase, preferably lipase. This method is preferably used since the substrate for the foregoing enzymes such as triglycerides, diglycerides, monoglycerides, fatty acids, fatty acid methyl esters and fatty acid ethyl esters are available in large quantities at low prices. As the chain isoprenoid alcohols, preferably used herein are geranyl geraniol, phytol and dihydrophytol while taking into consideration the industrial productivity and the bone metabolism-improving effect of the esters thus formed. When preparing the esters represented by Formula (I) and used in the present invention through the transesterification reactions, the reaction temperature preferably ranges from 20 to 80° C. and more preferably 30 to 70° C. Examples of solvents used include isooctane, hexane, heptane, octane, cyclohexane, chloroform, diethyl ether, isopropyl ether, ethyl acetate, propyl acetate, butyl acetate, toluene and xylene. Among them, preferably used herein are isooctane, hexane, heptane and octane. The amount of the enzyme used preferably ranges from 0.01 to 10% by mass and more preferably 0.1 to 5% by mass on the basis of the total mass of the reaction system. The reaction time preferably ranges from 0.1 to 48 hours and more preferably 0.5 to 24 hours. After the completion of the reaction, the resulting esters represented by Formula (I) and used in the present invention can be recovered by filtering the reaction system and purifying the same through, for instance, silica gel chromatography.

The isoprenoid esters incorporated into the improver for bone metabolism of the present invention are, as a whole, fat-soluble and therefore, they can favorably be incorporated into oily systems or emulsion systems. Moreover, it would be expected that they may be absorbed in the body along with oil components, when they are used, in particular, in the form of blend oils or foods prepared by adding oils and fats to food materials and therefore, such embodiments of the application thereof are quite preferred from the viewpoint of the absorbability. In this connection, it is a matter of course that one can enjoy quite excellent effects such as a bone metabolism-improving effect by increasing the amount of the isoprenoid esters to be incorporated into the agent.

The improver for bone metabolism of the present invention shows its effect when it is administered through oral and/or parenteral routes. In addition, the improver for bone metabolism of the present invention possesses a bone absorption-inhibitory effect and/or a bone formation-promoting effect and therefore, it is effective for preventing and/or treating various diseases in which any abnormality of bone metabolism is involved, but it is, in particular, used as an agent for preventing and/or treating osteoporosis. In this respect, the term "osteoporosis" used herein means a systemic osteopathy characterized by the reduction of the quantity of bone and the disorder or perturbation in the establishment of the bone fine structure and this accordingly makes the bone fragile and leads to an increase in the risk of fractured bone (WHO Consensus Development Conference; Am. J. Med. 1993, 94: 646). As a reason for this, it has been demonstrated that the balance between the bone absorption and the bone formation (osteogenesis) is broken down, the former is relatively superior to the latter and the bone is gradually reduced. The osteoporosis may roughly be divided into the protopathic osteoporosis and the deuteropathic osteoporosis, examples of the former include osteoporosis in the degenerative period such as osteoporosis after the menopause and senile osteoporosis and juvenile osteoporosis and examples of the latter include those caused subsequent to diseases of endocrine systems and metabolic disorders, those subsequent to collagen diseases, those subsequent to lying in bed over a long period of time and those caused due to the administration of glucocorticoid. The improver for bone metabolism of the present invention may be used for the prevention and/or treatment of any osteoporosis listed above. The term "use as a preventing agent" used herein means the use of the improver for bone metabolism of the present invention for the purpose of maintaining the healthy conditions of the bone while taking into consideration the reduction of the amount of bone observed after the menopause and in the senescence. The term "use as a therapeutic agent" used herein means the use of the improver for bone metabolism of the present invention for the purpose of inhibiting any further progress of the osteoporosis, which is in progress or a symptom of reduction in the amount of bone as the previous stage of the osteoporosis.

The improver for bone metabolism of the present invention can safely be administered to human and animals as, for instance, a pharmaceutical agent and a quasi-drug through oral and/or parenteral routes. Examples of parenteral administration include intravenous injection, intra-arterial injection, intramuscular injection, subcutaneous injection, intracutaneous injection, intraperitoneal injection, intra-spinal injection, epidural injection, percutaneous administration, administration through lung, pernasal administration, administration through intestine, administration through oral cavity and administration through mucous membranes and examples of dosage forms parenterally administered are injections, suppositories (such as those administered through anus, urethral suppositories, vaginal suppositories), liquids for external use (injections, gargles, mouth washes, fomentations, inhalants, sprays, aerosols, enema, paints, cleaning and wiping agents, disinfectants, nasal drops, and ear drops), patches, tapes for percutaneous absorption, agents externally applied to the skin and ointments (such as pastes, liniments, lotions). In addition, examples of orally administered pharmaceutical preparations are tablets for internal use (such as naked tablets, sugar-coated tablets, coating tablets, enteric coated tablets and chewable tablets), tablets administered through oral cavity (such as buccal preparations, sublingual tablets, troches and adhesive tablets), powders, capsules (such as hard capsules and soft capsules) and granules (such as coated granules, pills, troches, solutions or pharmaceutically acceptable sustained release preparations thereof). In addition, examples of orally administered solutions are mixture for internal use, shake mixtures, suspensions, emulsions, syrups, dry syrups, elixirs, infusions, decoctions and limonades.

These pharmaceutical preparations can be formulated into a medical drug together with pharmaceutically acceptable additives such as bases, carriers, excipients, binders, disintegrators, lubricants and/or coloring agents according to any preparation method known in the pharmaceutical technology and then administered to a patient.

Examples of such carriers and excipients used in these pharmaceutical preparations are lactose, glucose, sucrose, mannitol, potato starch, corn starch, calcium carbonate, calcium phosphate, calcium sulfate, crystalline cellulose, powdered glycyrrhiza and powdered gentian.

Examples of binders used in these pharmaceutical preparations are starches, tragacanth gum, gelatin, syrups, polyvinyl alcohols, polyvinyl ethers, polyvinyl pyrrolidones, hydroxypropyl cellulose, methyl cellulose, ethyl cellulose and carboxymethyl cellulose.

Examples of disintegrators used in these pharmaceutical preparations are starches, agar, powdered gelatin, sodium carboxymethyl cellulose, calcium carboxymethyl cellulose, crystalline cellulose, calcium carbonate, sodium hydrogen carbonate and sodium alginate.

Examples of lubricants used in these pharmaceutical preparations are magnesium stearate, talc, hydrogenated plant's oils and macrogol.

Examples of coloring agents used in these pharmaceutical preparations are those, which are allowed to incorporate into medical and pharmaceutical products.

Moreover, when preparing an injection, it is possible to optionally add other additives such as a pH controlling agent, a buffer, a stabilizer and/or solubilizing agent to thus give each corresponding injection according to the usual method.

When preparing a tablet and a granule, they may optionally be coated with at least one layer of sucrose, gelatin, hydroxypropyl cellulose, purified shellac, gelatin, glycerin, sorbitol, ethyl cellulose, hydroxypropyl cellulose, hydroxypropyl methyl cellulose, polyvinyl pyrrolidone, phthalic acid cellulose acetate, hydroxypropyl methyl cellulose phthalate, and methyl methacrylate, methacrylic acid polymers. Further, they may likewise be encapsulated into capsules of, for instance, ethyl cellulose or gelatin.

The external preparations may be in the form of, for instance, solid, semisolid, semisolid-like or liquid pharmaceutical preparations for percutaneous administration and administration through mucous membranes such as the administration through oral cavities or pernasal administration.

Examples of liquid pharmaceutical preparations are emulsified pharmaceutical preparations such as emulsions and lotions; tinctures for external use; and liquids for the administration through mucous membranes. These pharmaceutical preparations include diluents currently used such as ethanol, oily components and emulsifying agents.

Examples of semisolid pharmaceutical preparations are ointments such as oil-based ointments and hydrophilic ointments. These pharmaceutical preparations may comprise a currently used base or carrier such as water, vaseline, polyethylene glycol, oil components and/or surfactants.

Examples of semisolid or solid pharmaceutical preparations are hard plasters (such as gum plasters and plasters), films, tapes or pastings for percutaneous administration and administration through mucous membranes (such as the administration through oral cavities or pernasal administration) such as cataplasms. These pharmaceutical preparations may comprise currently used bases and/or carriers, for instance, rubber polymers such as naturally occurring rubber materials and synthetic rubber materials (for instance, butadiene rubber, SBR and SIS); sludge-forming agents such as gelatin, kaolin and zinc oxide; hydrophilic polymers such as sodium carboxymethyl cellulose and sodium polyacrylate; tacky producers such as acrylic resins and liquid paraffin; water; other oily components; and/or surfactants.

These pharmaceutical preparations may further comprise a stabilizer, an auxiliary agent such as a solubilizing agent or a percutaneous absorption-promoting agent, or other additives such as a perfume and/or an antiseptic.

Moreover, the improver for bone metabolism of the present invention may be used in combination with, for instance, other physiologically active components for the purpose of the improvement of various functions, in particular, for the synergistic improvement of the bone metabolism-improving effect, the supplementation of the bone metabolism-improving effect and/or the improvement of the absorbability. In particular, when using the agent of the present invention as a raw material and/or an additive for a food or a beverage or a feed, it is preferred to use the agent in combination with other physiologically active components. Such other physiologically active components are not restricted to specific ones insofar as the physiological functions thereof have been clearly elucidated and examples thereof include other improver for bone metabolisms, which may show a direct or indirect synergistic effect with the agent of the present invention; oily components for the improvement of the absorbability of the agent in the body and the improvement of the effect thereof; various kinds of vitamins, minerals and amino acids for the nutritional supplementation; and other physiologically active components.

Examples of other bone metabolism-improving components include calcium-containing substances such as calcium carbonate, calcium phosphate, calcium lactate, calcium gluconate, calcium aspartate and activated absorbable calcium; hormones such as estrogen and anti-estrogen; peptide hormones such as calcitonin; bis-phosphonates such as etidronate, clodronate and risedronate; vitamin Ds and derivatives thereof; vitamin Ks and derivatives thereof; and flavonoids such as flavone, catechin, quercetin, isoquercetin, leucoanthocyanidin, genistin, genistein, 6"-O-acetyl genistin, 6"-O-malonyl genistin, daidzin, daidzein, 6"-O-acetyl daidzin, 6"-O-malonyl daidzin, glycitin, glycitein, 6"-O-acetyl glycitin, 6"-O-malonyl glycitin, pueralin, quercetin, quenfelow, myroestrol, and Ipriflavone. These bone metabolism-improving components are preferably used in the present invention since they would show a synergistic effect with the isoprenoid esters used in the present invention. In the improver for bone metabolism of the present invention, the use of the chain isoprenoid fatty acid esters represented by Formula (I) and the foregoing other bone metabolism-improving components in combination would permit the detailed design of the bone metabolism-improving effect such as delicate or fine control of the degree of improvement and/or kinds of effect to be improved and therefore, desired effects can be imparted to the resulting agent of the present invention in response to each particular demand. In addition, it would be expected that the bone metabolism-improving effect is considerably reinforced due to the synergistic effect with other bone metabolism-improving components.

The oily components are not limited to specific ones, but examples thereof include those naturally occurring or prepared through chemical or enzymatic reactions such as MCT, MLCT, diglycerides and monoglycerides, and structured oils and fats whose fatty acid moieties are specially designed, in addition to oils and fats derived from plants such as soybean oil, rapeseed oil, cotton seed oil, sunflower oil, safflower oil, sesame oil, olive oil, linseed oil, rice bran oil, palm oil, cacao butter and kapok oil, and oils and fats derived from animals such as lard, tallow and fish oils.

Regarding the foregoing various kinds of vitamins, minerals and amino acids for the nutritional supplementation, examples thereof are not restricted to specific ones, but those specified in the Official Formulary of Food Additives are desirably used herein.

The foregoing other physiologically active substances may be those, which are fat-soluble and easily used in oil systems like the isoprenoid esters incorporated into the agent of the present invention and specific examples thereof are ferulic acids and derivatives thereof such as tocopherols, tocotrienols and γ-oryzanols; polyphenols such as lignans, sterois, phospholipids, oleuropein and tyrosol; and triterpenes such as oleanolic acid and maslinic acid.

The improver for bone metabolism of the present invention possesses bone metabolism-improving effects such as those described above. In other words, one can enjoy the foregoing bone metabolism-improving effects by directly or indirectly ingesting the improver for bone metabolism of the present invention. In addition, one can enjoy further improved such effects by continuously ingesting the agent of the present invention. The term "comprising as the active ingredien" used herein means that the agent of the present invention comprises the active ingredient in an amount sufficient for the achievement of the desired effect, but the amount of the isoprenoid esters to be incorporated into the improver for bone metabolism of the present invention is not unconditionally specified and may be appropriately be determined while taking into consideration various conditions and factors such as the kinds of the isoprenoid esters, the purpose of the use thereof (either prophylactic or therapeutic use), the administration period and amount of the esters, the age, sex and body weight of each particular subject to be treated, whether it is directly administered through the oral route or it is incorporated into other products as an ingredient as well as the desired degree of the foregoing effects. For instance, the content of the esters is not less than 0.00001% by mass, preferably not less than 0.0001% by mass, more preferably 0.001 to 99.99% by mass, further preferably 0.01 to 99.99% by mass, particularly preferably 0.1 to 99.99% by mass and most preferably 1 to 99.99% by mass, but the present invention is not restricted to the foregoing specific range at all.

Moreover, the desired amount of the isoprenoid esters used in the present invention for suitably accomplishing the bone metabolism-improving effect by ingesting the esters is not particularly restricted and may vary depending on various factors such as the manner of intake, and the sex, body weight and physical conditions of each particular subject, but it is, for instance, not less than 0.0001 g/day, preferably not less than 0.001 g/day and more preferably 0.01 g/day.

The improver for bone metabolism of the present invention is characterized in that it comprises an isoprenoid ester, can be used in any application including pharmaceutical agents and quasi-drugs and therefore, it may be used in wide variety of fields such as liquid foods, nutrients absorbed through intestine, health foods, foods and beverages such as foods for babies and little children and goods for beauty and health such as external preparations. These foods and beverages as well as goods for beauty and health are suitably used for routine administration of the improver for bone metabolism of the present invention and such an application of the agent is preferred since there is not any troublesome such as those observed for the administration of the pharmaceutical agents. The routine administration is preferred as a prophylactic use of the agent since such a manner of administration would permit the daily continuous administration thereof. The foods and beverages are in general administered through the oral route, while the products for beauty and health such as agents externally applied to the skin are in general administered percutaneously. In this regard, the amount of the improver for bone metabolism of the present invention to be incorporated into these products may vary depending on a variety of conditions such as the applications, the manner of administration, species, age, sex, body weight, the degree of symptoms and the conditions of health of the subject who ingests the products and therefore, it cannot unconditionally be specified, but it should be one sufficient for ensuring the effect required for the prevention and/or treatment of, for instance, osteoporosis.

The improver for bone metabolism of the present invention can be incorporated into a food or beverage as an ingredient to thus obtain a food or beverage having a bone metabolism-improving effect. Examples of foods and beverages are a variety of foods and beverages such as confectionery, processed foods, blend oils and fats, foods prepared by adding oils and fats to food materials, dairy products and beverages. In the present invention, the shapes and quality of the foods and beverages are not restricted to particular ones and they may have any shape such as solid-like, semisolid-like, gel-like, liquid-like and powdery shapes. Specific examples of foods and beverages to which the improver for bone metabolism of the present invention is applied are Japanese-style confections such as OKAKI, a rice cracker, a millet-and-rice cake and a bun with a bean-jam filling; a variety of European-style cakes such as cookies, biscuits, crackers, pies, castilla, doughnuts, custard puddings, sponge cakes, waffles, butter creams, custard creams, choux a la crème, chocolate, chocolate confectionery, caramel, candy, chewing gum, jelly, hot cakes, breads and buns; snack confectionery such as potato chips; frozen confectionery such as ice creams, ice candies and sherbet; refreshing beverages such as lactic acid beverages, lactobacillus-containing beverages, concentrated dairy beverages, fruit juice-containing beverages, flesh-containing beverages, functional beverages and carbonated beverages; table luxuries such as green tea, black tea, coffee, cocoa and beverages thereof; dairy products such as fermented milk, processed milk and cheese; processed foods derived from soybean such as soybean milk and soybean curd (TOFU); jams; fruits dipped in syrup; pastes such as flower paste, peanut pastes and fruit pastes; pickles or salted products; cereal products such as noodles and pastas; meat products such as ham, sausage, bacon, dry sausage, beef jerky and hamburg steak; processed sea foods such as fish meat ham, fish meat sausage, boiled fish paste, cylindrical fish paste and fish cakes; dried products such as dried fishes and shellfishes; pieces of boiled and dried fishes such as dried bonito, dried mackerel and dried horse mackerel; salted fishes such as salted and seasoned sea urchin eggs and salted and seasoned cuttlefishes; dried cuttlefishes; dried mirin-seasoned fishes or the like; smoked fish meat such as smoked salmon; foods boiled down in soy sauce such as those of laver, small fishes, shellfishes, edible wild plants, Cortinellus shiitake and sea tangles; retort foods such as curry and stew; various kinds of seasonings such as miso, soy sauce, sauce, catsup, bouillon, sauce for roast meat, curry roux, stock for stew, soup stock and stock for broth; cooked rice or the like; blend oils and fats; foods prepared by adding oils and fats to food materials such as margarine, shortening, mayonnaise and dressings; and a variety of foods for cooking in a microwave oven and frozen foods. Among these, preferred are cooked rice, a variety of seasonings, blend oils and fats and foods prepared by adding oils and fats to food materials such as margarine, shortening, mayonnaise and dressings while taking into consideration, in particular, the following facts such that the esters represented by Formula (I) are preferably derived from raw materials for oil stuffs, that the esters represented by Formula (I) are, on the whole, fat-soluble and that one should preferably ingest the esters continuously.

In this respect, it is sufficient that the content of the improver for bone metabolism or the isoprenoid esters in these foods and beverages is determined in proportion to, for instance, the desired bone metabolism-improving effect. For instance, the content of the esters represented by Formula (I) in the foods and beverages of the present invention preferably ranges from 0.0001 to 30% by mass, more preferably 0.001 to 20% by mass, further preferably 0.01 to 10% by mass, still further preferably 0.05 to 5% by mass and particularly preferably 0.1 to 3% by mass.

The intake of the food or beverage of the present invention may vary depending on various factors such as the manner of intake and the sex, body weight and physical conditions of each particular subject and is not restricted to any specific level, but it is, for instance, not less than 0.0001 g/day, preferably not less than 0.001 g/day, further preferably not less than 0.01 g/day, particularly preferably not less than 0.1 g/day, still further preferably 0.5 g/day, still particularly preferably not less than 1 g/day and most preferably not less than 2 g/day.

The improver for bone metabolism of the present invention can be incorporated into goods for beauty and health to thus give the same having a bone metabolism-improving effect. Such goods for beauty and health to which the improver for bone metabolism of the present invention can be applied are not restricted to specific ones, but preferred are those routinely and conveniently used such as drugs externally applied to the skin and bath medicines.

Dosage forms of the foregoing drugs externally applied to the skin are not restricted to specific ones and a part thereof will overlap specific examples of drugs and quasi-drugs, but specific examples thereof are milky lotions, creams, toilet waters, packs, cosmetics for washing, make-up cosmetics, dispersions and ointments. In addition to the foregoing, the drug externally applied to the skin may likewise comprise a functional component such as a blood circulation-improving agent, a humectant, an anti-oxidant, a bleaching ingredient, an ultraviolet absorber, a cell activator, an anti-inflammatory agent, an anti-bacterial agent, a percutaneous absorption accelerator, an extract derived from an animal and/or an extract derived from a plant.

In the present invention, the isoprenoid esters are preferably used in, for instance, drugs externally applied to the skin and bath medicines since these substances are percutaneously absorbed and these drugs may conveniently be used.

It is sufficient that the content of the improver for bone metabolism of the present invention or the isoprenoid esters in the articles for beauty and health such as drugs externally applied to the skin may be determined while taking into consideration the desired extent of the bone metabolism-improving effect. For instance, the drug externally applied to the skin according to the present invention preferably comprises the esters represented by Formula (I) in an amount preferably ranges from 0.0001 to 99.99% by mass, more preferably 0.001 to 90% by mass, still more preferably 0.01 to 70% by mass, further preferably 0.05 to 50% by mass and particularly preferably 0.1 to 30% by mass.

The amount of the drug externally applied to the skin according to the present invention may vary depending on various factors such as the sex, body weight and physical conditions of each particular subject and cannot thus unconditionally be specified, but it is, for instance, not less than 0.0001 g/day, preferably not less than 0.001 g/day, further preferably not less than 0.01 g/day, particularly preferably not less than 0.1 g/day, still further preferably 0.5 g/day, still particularly preferably not less than 1 g/day and most preferably not less than 2 g/day.

The present invention relates to a raw material for an improver for bone metabolism, which comprises at least one member selected from the group consisting of chain isoprenoid fatty acid esters represented by Formula (I). In this case, the isoprenoid esters are not particularly limited in their origins and either naturally occurring ones or artificially synthesized ones may suitably be used in the present invention, but the purity of the isoprenoid esters is preferably as high as possible since they are used for preparing an improver for bone metabolism. The use of the esters having high purity would permit the considerable improvement of the bone metabolism-improving effect and the considerable reduction of the content of impurities. More specifically, the use of such highly purified esters would contribute to the elimination of the occurrence of any unpredictable risks such as side effects due to, for instance, the presence of impurities, the elimination of any unpredictable troubles possibly encountered when an improver for bone metabolism and the improvement of, for instance, the quality of the product such as the improvement of the handling properties. For this reason, the isoprenoid esters preferably have purity as high as possible. When the purity of the isoprenoid ester becomes high because of the isolation-purification treatment thereof, the esters thus obtained are, on the whole, in the form of white or colorless solids, semisolids or liquids and therefore, they can suitably be incorporated into, for instance, improver for bone metabolisms without adversely affecting the color of the bone agent peculiar thereto. As has been described above, the purity of the isoprenoid ester used in, for instance, the raw material for an improver for bone metabolism is preferably as high as possible, but it cannot unconditionally be specified and may appropriately be determined in due consideration of various factors such as the kinds of isoprenoid esters used, the purpose of applications (either prophylactic or therapeutic use), the routes of administration, the preparation methods and the production cost. For instance, the content of the esters in the raw material for an improver for bone metabolism is not less than 0.001% by mass, preferably 0.01 to 99.99% by mass, further preferably 0.1 to 99.99% by mass, more preferably 1 to 99.99% by mass, further preferably 10 to 99.99% by mass, particularly preferably 25 to 99.99% by mass and most preferably 50 to 99.99% by mass, but the present invention is not restricted to the foregoing specific range at all.

The raw material for preparing an improver for bone metabolism, detailed above, according to the present invention may be used in or incorporated into drugs and quasi-drugs, but may likewise be used in other various applications. Examples of such other applications are not restricted to specific ones in as much as they possess bone metabolism-improving effects, include foods and beverages, feeds, cosmetics and bath cosmetics and may favorably be used in either of these products.

The present invention relates to an improver for bone metabolism comprising an isoprenoid ester. The isoprenoid ester is excellent, in particularly, in the bone metabolism-improving effect such as the bone absorption-inhibitory action and the osteogenesis-promoting action and can easily be prepared. In addition the ester does not suffer from any problem concerning safety and is excellent in the absorbability because of its high fat-solubility. The improver for bone metabolism of the present invention can be used for preventing and/or treating any osteopathy such as osteoporosis and further it can likewise routinely be used in the form of foods and beverages and drugs externally applied to the skin, in addition to the drugs.

EXAMPLES

The present invention will hereunder be described with reference to the following Examples, but the present invention is not restricted to these specific Examples at all.

The following raw materials used in the following Examples were purchased from the Company specified below: geraniol (available from WAKO Pure Chemical Co., Ltd.); farnesol (available from Sigma Company); geranyl geraniol (available from Sigma Company); phytol (available from WAKO Pure Chemical Co., Ltd.); tristearin (available from Sigma Company); triolein (available from WAKO Pure Chemical Co., Ltd.); tri-γ-linolein (available from FUNAKOSHI Co., Ltd.); ethyl ester of conjugated linoleic acid (available from FUNAKOSHI Co., Ltd.); ethyl ester of eicosapentaenoic acid (available from WAKO Pure Chemical Co., Ltd.); and tridocosahexaenoin (available from FUNAKOSHI Co., Ltd.). Dihydrophytol was prepared by reducing phytol according to the method described in the literature (J. Org. Chem., 1993, 58: 5285-5287).

Example 1

Geranyl-Geranyl Stearate

There were dissolved, in 1 g of isooctane, 100 mg of geranyl geraniol and 900 mg of tristearin, followed by the addition of lipase in an amount of 1% relative to the total amount of the resulting solution and then stirring the mixture at 60° C. for 3 hours. After confirming whether the reaction system reached its equilibrium state or not by the GC technique, the reaction solution was diluted by the addition of hexane to the solution in an amount of 10 times the volume thereof, followed by the removal of the lipase from the reaction solution through filtration and then the removal of the hexane through distillation to thus give a crude reaction product. The crude product was purified by silica gel column chromatography to give 137 mg of geranyl-geranyl stearate.

Example 2

Geranyl-Geranyl Oleate

There were dissolved, in 1 g of isooctane, 100 mg of geranyl geraniol and 900 mg of triolein, followed by the addition of lipase in an amount of 1% relative to the total amount of the resulting solution and then stirring the mixture at 60° C. for 3 hours. After confirming whether the reaction system reached its equilibrium state or not by the GC technique, the reaction solution was diluted by the addition of hexane to the solution in an amount of 10 times the volume thereof, followed by the removal of the lipase from the reaction solution through filtration and then the removal of the hexane through distillation to thus give a crude reaction product. The crude product was purified by silica gel column chromatography to give 137 mg of geranyl-geranyl oleate.

Example 3

Geranyl-Geranyl γ-Linolenate

There were dissolved, in 1 g of isooctane, 100 mg of geranyl geraniol and 900 mg of tri-γ-linolein, followed by the addition of lipase in an amount of 1% relative to the total amount of the resulting solution and then stirring the mixture at 60° C. for 3 hours. After confirming whether the reaction system reached its equilibrium state or not by the GC technique, the reaction solution was diluted by the addition of hexane to the solution in an amount of 10 times the volume thereof, followed by the removal of the lipase from the reaction solution through filtration and then the removal of the hexane through distillation to thus give a crude reaction product. The crude product was purified by silica gel column chromatography to give 143 mg of geranyl-geranyl γ-linolenate.

Example 4

Geranyl-Geranyl Conjugated Linoleate

There were dissolved, in 1 g of isooctane, 100 mg of geranyl geraniol and 300 mg of ethyl ester of conjugated linoleic acid, followed by the addition of lipase in an amount of 1% relative to the total amount of the resulting solution and then stirring the mixture at 60° C. for 24 hours. After confirming whether the reaction system reached its equilibrium state or not by the GC technique, the reaction solution was diluted by the addition of hexane to the solution in an amount of 10 times the volume thereof, followed by the removal of the lipase from the reaction solution through filtration and then the removal of the hexane through distillation to thus give a crude reaction product. The crude product was purified by silica gel column chromatography to give 118 mg of geranyl-geranyl conjugated linoleate.

Example 5

Geranyl Eicosapentaenoate

There were dissolved, in 1 g of isooctane, 100 mg of geraniol and 900 mg of ethyl ester of eicosapentaenoic acid, followed by the addition of lipase in an amount of 1% relative to the total amount of the resulting solution and then stirring the mixture at 60° C. for 24 hours. After confirming whether the reaction system reached its equilibrium state or not by the GC technique, the reaction solution was diluted by the addition of hexane to the solution in an amount of 10 times the volume thereof, followed by the removal of the lipase from the reaction solution through filtration and then the removal of the hexane through distillation to thus give a crude reaction product. The crude product was purified by silica gel column chromatography to give 122 mg of geranyl eicosapentaenoate.

Example 6

Farnesyl Eicosapentaenoate

There were dissolved, in 1 g of isooctane, 100 mg of farnesol and 750 mg of ethyl ester of eicosapentaenoic acid, followed by the addition of lipase in an amount of 1% relative to the total amount of the resulting solution and then stirring the mixture at 60° C. for 24 hours. After confirming whether the reaction system reached its equilibrium state or not by the GC technique, the reaction solution was diluted by the addition of hexane to the solution in an amount of 10 times the volume thereof, followed by the removal of the lipase from the reaction solution through filtration and then the removal of the hexane through distillation to thus give a crude reaction product. The crude product was purified by silica gel column chromatography to give 107 mg of farnesyl eicosapentaenoate.

Example 7

Geranyl-Geranyl Eicosapentaenoate

There were dissolved, in 1 g of isooctane, 100 mg of geranyl geraniol and 600 mg of ethyl ester of eicosapentaenoic acid, followed by the addition of lipase in an amount of 1% relative to the total amount of the resulting solution and then stirring the mixture at 60° C. for 24 hours. After confirming whether the reaction system reached its equilibrium state or not by the GC technique, the reaction solution was diluted by the addition of hexane to the solution in an amount of 10 times the volume thereof, followed by the removal of the lipase from the reaction solution through filtration and then the removal of the hexane through distillation to thus give a crude reaction product. The crude product was purified by silica gel column chromatography to give 102 mg of geranyl-geranyl eicosapentaenoate.

Example 8

Phytyl Eicosapentaenoate

There were dissolved, in 1 g of isooctane, 100 mg of phytol and 600 mg of ethyl ester of eicosapentaenoic acid, followed by the addition of lipase in an amount of 1% relative to the total amount of the resulting solution and then stirring the mixture at 60° C. for 24 hours. After confirming whether the reaction system reached its equilibrium state or not by the GC technique, the reaction solution was diluted by the addition of hexane to the solution in an amount of 10 times the volume thereof, followed by the removal of the lipase from the reaction solution through filtration and then the removal of the hexane through distillation to thus give a crude reaction product. The crude product was purified by silica gel column chromatography to give 94 mg of phytyl eicosapentaenoate.

Example 9

Dihydrophytyl Eicosapentaenoate

There were dissolved, in 1 g of isooctane, 100 mg of dihydrophytol and 600 mg of ethyl ester of eicosapentaenoic acid, followed by the addition of lipase in an amount of 1% relative to the total amount of the resulting solution and then stirring the mixture at 60° C. for 24 hours. After confirming whether the reaction system reached its equilibrium state or not by the GC technique, the reaction solution was diluted by the addition of hexane to the solution in an amount of 10 times the volume thereof, followed by the removal of the lipase from the reaction solution through filtration and then the removal of the hexane through distillation to thus give a crude reaction product. The crude product was purified by silica gel column chromatography to give 94 mg of dihydrophytyl eicosapentaenoate.

Example 10

Geranyl-Geranyl Docosahexaenoate

There were dissolved, in 1 g of isooctane, 100 mg of geranyl geraniol and 900 mg of tridocosahexaenoin, followed by the addition of lipase in an amount of 1% relative to the total amount of the resulting solution and then stirring the mixture at 60° C. for 3 hours. After confirming whether the reaction system reached its equilibrium state or not by the GC technique, the reaction solution was diluted by the addition of hexane to the solution in an amount of 10 times the volume thereof, followed by the removal of the lipase from the reaction solution through filtration and then the removal of the hexane through distillation to thus give a crude reaction product. The crude product was purified by silica gel column chromatography to give 173 mg of geranyl-geranyl docosahexaenoate.

Example 11

Test for Confirming Bone Absorption-Inhibitory Action Using Cell Co-Cultivation System The test for the confirmation of the bone absorption-inhibitory action of the isoprenoid ester was carried out according to the method disclosed in the literature (Endocrinology, 1988, 123: 2600). The method will be outlined below:

(Preparation of Osteoblast)

Stroma cells collected from the skull-caps of two-week-old mice according to the method disclosed in the literature (Endocrinology, 1988, 123: 2600) were dispersed in a 10% fetal bovine serum-containing culture base liquid ($\alpha$-MEM; available from Gibco Company) to a cell density of $5 \times 10^4$ cells/mL.

(Preparation of Spleen Cells)

Spleen cells collected from the spleen of 6-week-old ddy male mice according to the method disclosed in the literature (Proc. Natl. Acad. Sci. USA, 1983, 80: 5583) were dispersed in a 10% fetal bovine serum-containing culture base liquid ($\alpha$-MEM; available from Gibco Company) to a cell density of $5 \times 10^5$ cells/mL.

(Co-Cultivation Method)

The co-cultivation was carried out in a 5% $CO_2$-containing atmosphere at a temperature of 37° C. using a 10% FBS (fetal bovine serum)-containing culture base liquid ($\alpha$-MEM; available from Gibco Company). Osteoblast cells were inoculated on a 24-well petri dish at a cell density of $5 \times 10^4$ cells/mL/well, spleen cells were then inoculated thereon at a cell density of $5 \times 10^5$ cells/mL/well after one day and a solution of a test substance, which had been dissolved in DMSO in a concentration of 10-2M, was then added to each well in such a manner that the concentration of the test substance was equal to 10 $\mu$M. These cells were cultivated in the presence of 10 nM Calcitriol and 100 nM Dexamethasone over 2 weeks while defining the day on which the spleen cells were inoculated as $0^{th}$ day. In this respect, the culture medium was replaced with fresh one twice a week. After two weeks, the activity of the tartrate-resistant acid phosphatase (hereunder referred to as "TRACP") in the cell layer was determined, which served as a parameter indicating the number of osteoclasts in the layer.

(Determination of the TRACP Activity)

In the determination of the TRACP activity, there was used a kit of acid phosphatase KII-WAKO (available from WAKO Pure Chemical Co., Ltd.). The culture medium was removed from the Petri dish, 500 μL each of a substrate was added to each well, the resulting cell suspension was heated at 37° C. for 15 minutes, followed by the addition of 500 μL each of a color developing liquid and the determination of the absorbance at a wavelength of 570 nm. The TRACP activity corresponding to each absorbance thus measured was determined using a calibration curve prepared in advance. The results thus obtained are listed in the following Table 1.

TABLE 1

| Ex. No. | Test Substance | TRACP Act. (KA-U/well) | Judged Efficacy** |
|---|---|---|---|
| Cont. | None | 102.8 ± 12.6 | — |
| 1 | Geranyl-geranyl stearate | 25.3 ± 5.2 | ⊚ |
| 2 | Geranyl-geranyl oleate | 16.8 ± 3.4 | ⊚ |
| 3 | Geranyl-Geranyly γ-Linolenate | 21.7 ± 4.9 | ⊚ |
| 4 | Geranyl Eicosapentaenoate | 87.4 ± 10.3 | Δ |
| 5 | Farnesyl Eicosapentaenoate | 96.9 ± 12.7 | Δ |
| 6 | Geranyl-Geranyl Eicosapentaenoate | 9.7 ± 1.4 | ⊚ |
| 7 | Phytyl Eicosapentaenoate | 84.2 ± 7.1 | ○ |
| 8 | Dihydrophytyl Eicosapentaenoate | 83.4 ± 9.4 | ○ |
| 9 | Geranyl-Geranyl Docosahexaenoate | 18.5 ± 5.8 | ⊚ |
| 1* | Vitamin K1 | 88.5 ± 8.1 | ○ |
| 2* | Vitamin K2 (MK-4) | 20.3 ± 4.1 | ⊚ |
| 3* | Vitamin K3 | 87.9 ± 10.2 | ○ |

*Comparative Example
**The evaluation standard of the efficiency is as follows (p means the ratio of risk in the t-test relative to the control): ⊚: The test substance shows a considerable inhibitory effect (p < 0.01); ○: The test substance shows an inhibitory effect (p < 0.05); Δ: The test substance shows only slight or no inhibitory effect (there is not observed any significant difference); X: The test substance shows a bone absorption-promoting effect (there is observed a negativesignificant difference)

As will be clear from the data listed in Table 1, when comparing with the results observed for the control group (free of any added test substance), there were observed significant bone absorption-inhibitory effects in the geranyl-geranyl fatty acid ester-, phytyl fatty acid ester- and dihydrophytyl fatty acid ester-added groups. However, there were observed almost no bone absorption-inhibitory effect in the geranyl fatty acid ester- and farnesyl fatty acid ester-added groups. Thus, it was found that the bone absorption-inhibitory effect was conspicuous in the isoprenoid fatty acid esters having an isoprene unit of 4 (n=4 in the structural formula (I)).

Example 12

Test for Confirming Bone Formation-Promoting Effect in Cell Culture System

In this Example, there were examined the effects of the chain isoprenoid fatty acid esters on the differentiation and calcium-accumulation of MC3T3-E1 cells or the osteoblasts derived from the skull-caps of mice. A culture medium was added to a 6-well plate in an amount of 2 mL/well, a desired number of MC3T3-E1 cells was inoculated on the medium and the cells were cultivated in a 10% fatal bovine serum-containing base culture liquid (α-MEM, available from Gibco Company) at 37° C. in an atmosphere of 5% $CO_2$. On the day subsequent to the initiation of the cultivation, the culture medium was replaced with the fresh one and simultaneously a solution containing each test sample (the chain isoprenoid fatty acid esters obtained in Preparation Examples 1 to 9) was admixed with and added to the culture medium in an amount of 10 μM for the determination of the cell growth rate and 2.5 μM for the determination of the alkali phosphatase (ALP) activity and the cultivation was continued. The cells for the cell growth rate determination were recovered after 3 days from the initiation of the cultivation and the number of viable cells was counted to determine the cell growth rate. Regarding the other cells, the medium was replaced with fresh one on $5^{th}$ day of cultivation, the test sample-containing solution was again added and the alkali phosphatase (ALP) activity was determined after the cultivation over one week.

(Cell Growth Rate)

The cell growth rate was calculated as a value relative to the cell growth rate observed for the control (free of any added test sample), which was defined to be 100. The results thus obtained are listed in the following Table 2.

TABLE 2

| Ex. No. | Test Substance | Cell Growth Rate (%) |
|---|---|---|
| Control | None | 100.0 |
| 1 | Geranyl-geranyl stearate | 102.9 |
| 2 | Geranyl-geranyl oleate | 108.3 |
| 3 | Geranyl-Geranyl γ-Linolenate | 111.4 |
| 4 | Geranyl-Geranyl Conjugated Linoleate | 120.1 |
| 5 | Geranyl Eicosapentaenoate | 121.4 |
| 6 | Farnesyl Eicosapentaenoate | 115.6 |
| 7 | Geranyl-Geranyl Eicosapentaenoate | 107.8 |
| 8 | Phytyl Eicosapentaenoate | 123.4 |
| 9 | Dihydrophytyl Eicosapentaenoate | 118.9 |
| 10 | Geranyl-Geranyl Docosahexaenoate | 104.8 |
| 1* | Vitamin K1 | 69.3 |
| 2* | Vitamin K2 (MK-4) | 32.4 |
| 3* | Vitamin K3 | 0.0 |

The data listed in Table 2 suggest that the chain isoprenoid fatty acid esters used in the present invention show effects of promoting the proliferation of the cells: MC3T3-E1 osteoblasts although there is not observed any significant difference. It was also found that vitamin Ks showed cell growth-inhibitory effects or cytotoxicity, while the esters were quite promising substances because of their ability of promoting osteoblast involved in the bone formation and high safety.

(Determination of Alkaline Phosphatase (ALP) Activity)

In these experiments, there was used a kit for Alkaline Phospha K-Test WAKO (available from WAKO Pure Chemical Co., Ltd.). A sample used was a suspension of cells obtained by cultivating the same in the presence of each test substance added. A substrate (150 μL) was added to 10 μL of each sample followed by heating at 37° C. for 15 minutes, the addition of 150 μL of a color-developing liquid and determination of the absorbance at 570 nm. The ALP activity corresponding to each absorbance thus measured was determined using a calibration curve prepared in advance. The results thus obtained are listed in the following Table 3.

TABLE 3

| Ex. No. | Test Substance | ALP Act. (KA-U/well) | Judged Efficacy** |
|---|---|---|---|
| Cont. | None | 71.6 ± 4.6 | — |
| 1 | Geranyl-geranyl stearate | 80.1 ± 5.2 | ○ |
| 2 | Geranyl-geranyl oleate | 82.8 ± 6.7 | ○ |
| 3 | Geranyl-Geranyl γ-Linolenate | 84.4 ± 5.1 | ⊚ |
| 4 | Geranyl-geranyl conjugated linoleate | 88.3 ± 4.8 | ⊚ |
| 5 | Geranyl Eicosapentaenoate | 87.2 ± 10.6 | ○ |
| 6 | Farnesyl Eicosapentaenoate | 85.4 ± 8.4 | ○ |
| 7 | Geranyl-Geranyl Eicosapentaenoate | 123.5 ± 7.3 | ⊚ |
| 8 | Phytyl Eicosapentaenoate | 114.6 ± 7.7 | ⊚ |
| 9 | Dihydrophytyl Eicosapentaenoate | 118.7 ± 8.9 | ⊚ |
| 10 | Geranyl-Geranyl Docosahexaenoate | 89.8 ± 6.1 | ⊚ |
| 1* | Vitamin K1 | 76.1 ± 4.9 | Δ |
| 2* | Vitamin K2 (MK-4) | 78.6 ± 3.2 | ○ |
| 3* | Vitamin K3 | 91.2 ± 11.0 | ○ |

*Comparative Example
**The evaluation standard of the efficiency is as follows (p means the ratio of risk in the t-test relative to the control): ⊚: The test substance shows a considerable inhibitory effect ($p < 0.01$); ○: The test substance shows an inhibitory effect ($p < 0.05$); Δ: The test substance shows only slight or no inhibitory effect (there is not observed any significant difference); X: The test substance shows a bone absorption-promoting effect (there is observed a negativesignificant difference).

The results of the foregoing tests clearly indicate that the ALP activities observed for the chain isoprenoid fatty acid ester-added groups are significantly increased as compared with the control group (free of any added test substance) and therefore, the isoprenoid esters possess bone formation-promoting effects. In particular, the ALP activities are considerably increased in the groups containing isoprenoid γ-linolenic acid ester having n-6 type fatty acid side chains; isoprenoid eicosapentaenoic acid ester and isoprenoid docosahexaenoic acid ester having n-3 type fatty acid side chains; and isoprenoid conjugated linoleate having conjugated fatty acid side chains.

Example 13

Test for Acute Toxicity

The acute toxicity test was carried out according to the following method. Whister female rats (6-week-old, average body weight: 160 g) were previously kept for one week using a powdery blend feed having an AIN-93 composition, divided into three groups (each group containing 10 animals) in such a manner that the average body weight was uniform and the groups were specified as the orally administered group, the subcutaneously administered group and the intraperitoneally administered group, in the following tests. Geranyl-geranyl eicosapentaenoate prepared according to the procedures used in Example 5 was dissolved in cotton seed oil and administered to the foregoing animals through the corresponding administration routes in an amount of 2000 mg/kg (body weight). Subsequently, these animals were kept using a powdery blend feed having an AIN-93 composition to thus observe the prognostic conditions of the animals over 2 weeks after the administration and after 2 weeks, these animals were anatomized to thus inspect the animals for conditions of internal organs thereof.

As a result, it was found that any animal was not killed in either of the groups after 2 weeks from the administration and the anatomical findings of the internal organs were normal. This clearly indicates that the LD50 value of geranyl-geranyl eicosapentaenoate was higher than 2000 mg/kg (body weight) and that the ester was quite excellent in safety.

Example 14

Tablet

| | |
|---|---|
| Geranyl-geranyl oleate of Example 2 | 1.0 mg |
| Lactose | 94.0 mg |
| Corn Starch | 34.0 mg |
| Crystalline Cellulose | 20.0 mg |
| Calcium having activated absorbability (derived from oyster shell) | 10.0 mg |
| Vitamin D3 | 20 IU |
| Magnesium Stearate | 1.0 mg |

The foregoing components were sufficiently admixed together in a mixing ratio specified above and the resulting mixture was compressed into tablets.

Example 15

Powder

| | |
|---|---|
| Geranyl-geranyl γ-linoleate prepared in Example 3 | 2.0 mg |
| Lactose | 981.0 mg |
| Hydroxypropyl cellulose | 4.0 mg |
| Soft anhydrous silicic acid | 5.0 mg |

First geranyl-geranyl γ-linoleate and lactose were sufficiently admixed together in the mixing ratio specified above and then hydroxypropyl cellulose was added to the resulting mixture and then the mixture was granulated. After the granulated mixture was dried, the particle size thereof was controlled and soft anhydrous silicic acid was added to and sufficiently admixed with the particles to thus give a powder.

Example 16

Capsule

| | |
|---|---|
| Geranyl-geranyl conjugated linoleate prepared in Example 4 | 150.0 mg |
| Lactose | 70.0 mg |
| Corn starch | 38.0 mg |
| Magnesium stearate | 2.0 mg |

The foregoing components were sufficiently admixed together in the mixing ratio specified above and the resulting mixture was encapsulated into capsules.

Example 17

Soft Capsule

| | |
|---|---|
| Phytyl eicosapentaenoate prepared in Example 8 | 50.0 mg |
| Purified soybean oil | 130.0 mg |
| Tocopherol | 20.0 mg |

The foregoing components were sufficiently admixed together in the mixing ratio specified above and the resulting mixture was encapsulated to give soft capsules.

Example 18

Injection

| | |
|---|---|
| Geranyl-geranyl eicosapentaenoate prepared in Example 7 | 10.0 mg |
| Polyoxyethylene-hardened castor oil | 200.0 mg |
| Anhydrous ethanol | q.s. |

First geranyl-geranyl eicosapentaenoate was sufficiently admixed with polyoxyethylene-hardened castor oil in the mixing ratio or amounts specified above and then anhydrous ethanol was added to the resulting mixture in such an amount that the total volume of the resulting mixture was equal to 1 ml to thus give an injection.

Example 19

Gel-Like Ointment

| | |
|---|---|
| Carboxy vinyl polymer | 1.0 g |
| 1,3-Butylene glycol | 10.0 g |
| Geranyl-geranyl docosahexaenoate prepared in Example 10 | 0.1 g |
| Triethanolamine | 1.0 g |
| Purified water | 87.9 g |

The foregoing components were uniformly admixed together to give a gel-like ointment.

Example 20

Fatty Acid Geranyl-Geranyl Ester-Containing Blend Oil and Fats

Geranyl geraniol was dissolved in purified soybean oil in an amount of 0.1 g relative to 1000 g of the latter, NOVOZYME (available from Novo Company) was added to the resulting solution in an amount of 1% on the basis of the total amount of the mixture and then the mixture was stirred at 60° C. for 3 hours using a propeller stirring machine. After the completion of the reaction, the reaction system was diluted by the addition of hexane in an amount of 10 times the volume of the system, the lipase was removed from the diluted reaction system and then the hexane was completely distilled off through vacuum distillation to thus give fatty acid geranyl-geranyl ester-containing blend oils and fats. The content of the fatty acid geranyl-geranyl ester in the blend oils and fats was found to be 0.0187%. The resulting blend oils and fats were excellent in the taste and palatability and could be used like the usual purified soybean oil.

Example 21

Blend Oils and Fats Having High Chain Isoprenoid Fatty Acid Ester

The isoprenoid fatty acid esters prepared according to the same procedures used in Examples 2, 4 and 7 were added to and dissolved in cotton seed oil and sesame oil in amounts (mass ratio) of 1000 ppm and 10000 ppm, respectively to thus prepare 12 samples, in all, of blend oils and fats containing chain isoprenoid fatty acid esters. As a result, either of these blend oils and fats was excellent in the taste and palatability and could be used like the usual oils and fats to which any chain isoprenoid fatty acid ester was not particularly added.

Example 22

Dressing

| | |
|---|---|
| Water | 46.6 g |
| Xanthane gum | 0.1 g |
| Fructose, glucose, liquid sugar | 5.0 g |
| Common salt | 5.0 g |
| MSG | 0.3 g |
| Rice vinegar (having an acidity of 10%) | 10.0 g |
| Pepper | q.s. |
| Geranyl-geranyl γ-linoleate prepared in Example 3 | 0.1 g |
| MLCT | 32.9 g |

The foregoing raw materials other than MLCT were introduced into a container equipped with a stirring machine and capable of being heated in a mixing ratio specified above, followed by heating the mixture till the temperature of the mixture reached to 90° C. with stirring the same at 100 rpm using a propeller stirring machine and then stirring the mixture for 25 minutes while maintaining the temperature thereof at 90° C. Thereafter, the mixture was cooled down till the temperature of the mixture reached to 20° C. and admixed with MLCT to thus give a dressing.

Example 23

Margarine

| | |
|---|---|
| Rapeseed oil | 42.0 g |
| Hardened rapeseed oil | 42.0 g |
| Water | 14.0 g |
| Common salt | 0.5 g |
| Lecithin | 0.5 g |
| Monoglyceride | 0.4 g |
| Geranyl eicosapentaenoate prepared in Example 5 | 0.1 g |
| Farnesyl eicosapentaenoate prepared in Example 6 | 0.1 g |
| Geranyl-geranyl eicosapentaenoate prepared in Example 7 | 0.1 g |
| Phytyl eicosapentaenoate prepared in Example 8 | 0.1 g |
| Dihydrophytyl eicosapentaenoate prepared in Example 9 | 0.1 g |
| Perfume | q.s. |
| Carotene | Trace Amt. |

The foregoing raw materials were admixed together according to the usual method and then subjected to a quenching-kneading treatment in a combining machine to give margarine.

Example 24

Mayonnaise

| | |
|---|---|
| Soybean salad oil | 74.0 g |
| Water | 8.4 g |
| Sugar | 1.0 g |
| Sodium glutamate | 0.3 g |
| Powdered mustard | 0.3 g |
| Common salt | 1.0 g |
| Rice vinegar | 4.0 g |
| Geranyl-geranyl docosahexaenoate prepared according to the same procedures used in Example 10 | 1.0 g |
| Egg yolk containing added salt | 10.0 g |

First the foregoing raw materials other than soybean salad oil and salt-containing egg yolk were admixed together with stirring in a mixing ratio specified above, the resulting mixture was heated up to 90° C. and stirred for 25 minutes while maintaining the temperature thereof at 90° C. After cooling the mixture to 20° C., the soybean salad oil and salt-containing egg yolk were incorporated into the mixture and the resulting mixture was stirred under reduced pressure to give mayonnaise.

Example 25

Refreshing Beverage

| | |
|---|---|
| Geranyl-geranyl stearate prepared in Example 1 | 0.5 g |
| Honey | 15.0 g |
| Citric acid | 0.1 g |
| dl-Malic acid | 0.1 g |
| D-Sorbitol liquid (70%) | 10.0 g |
| Sodium benzoate | 0.1 g |
| Perfume | q.s. |
| Purified water | ad. 100 g |

The foregoing raw materials were uniformly admixed together to give a drink for health.

One can enjoy a quite excellent bone metabolism-improving effect of the chain isoprenoid fatty acid esters when using the improver for bone metabolism of the present invention. The chain isoprenoid fatty acid esters are excellent, in particular, in the bone absorption-inhibitory and/or bone formation-promoting effects and therefore, one can enjoy, in particular, these effects through the use of the improver for bone metabolism of the present invention. Moreover, the chain isoprenoid fatty acid esters usable herein may be naturally occurring ones or artificially synthesized ones. These esters are fat-soluble and quite safe and therefore, the present invention permits the enjoyment of the bone metabolism-improving effect and the present invention also permits the preparation of an improver for bone metabolism excellent in the absorbability and safety at a low price.

What is claimed is:

1. A method for improving bone metabolism comprising administering to a subject in need thereof, as the active ingredient, chain isoprenoid fatty acid esters represented by the following general formula (I):

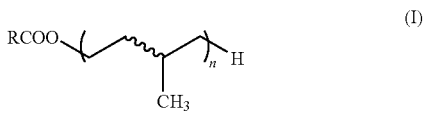

wherein R represents an arbitrary hydrocarbon functional group,
the wavy line means a single or double bond,
n represents an integer ranging from 1 to 14, provided that when n is 2 or higher, the wavy lines may be the same or different, and
the fatty acid constituting the chain isoprenoid fatty acid esters has 2 to 30 carbon atoms.

2. The method of claim 1, wherein the fatty acid constituting the chain isoprenoid fatty acid esters is a linear unsaturated fatty acid.

3. The method of claim 2, wherein the linear unsaturated fatty acid constituting the chain isoprenoid fatty acid esters is a member selected from the group consisting of n-6 type unsaturated fatty acids, n-3 type unsaturated fatty acids and conjugated fatty acids.

4. The method of claim 3, wherein the n-6 type unsaturated fatty acid constituting the chain isoprenoid fatty acid esters is a member selected from the group consisting of linoleic acid, γ-linolenic acid, bis-homo-γ-linolenic acid and arachidonic acid.

5. The method of claim 3, wherein the n-3 type unsaturated fatty acid constituting the chain isoprenoid fatty acid esters is a member selected from the group consisting of α-linolenic acid, stearidonic acid, eicosatetraenoic acid, eicosapentaenoic acid, docosapentaenoic acid and docosahexaenoic acid.

6. The method of claim 3, wherein the conjugated fatty acid constituting the chain isoprenoid fatty acid esters is a member selected from the group consisting of conjugated linoleic acid and α-eleostearic acid.

7. A method for improving bone metabolism comprising administering to a subject in need thereof, as the active ingredient, chain isoprenoid fatty acid esters represented by the following general formula (I):

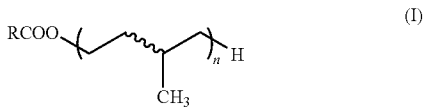

wherein R represents a hydrocarbon functional group,
the wavy line means a single or double bond,
the wavy lines may be the same or different, and
n is 2 to 4.

8. A method for improving bone metabolism comprising administering to a subject in need thereof, as the active ingredient, chain isoprenoid fatty acid esters represented by the following general formula (I):

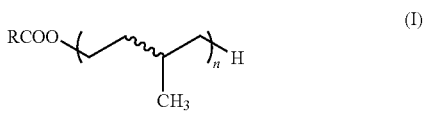

wherein R represents a hydrocarbon functional group, the wavy line means a single or double bond, n represents an integer ranging from 1 to 14, provided that when n is 2 or higher, the wavy lines may be the same or different, and the alcohol constituting the chain isoprenoid fatty acid esters is one derived from vegetable oils and fats.

9. The method of claim 3, wherein the alcohol constituting the chain isoprenoid fatty acid esters is a member selected from the group consisting of geraniol, farnesol, geranyl geraniol, phytol and dihydrophytol.

* * * * *